United States Patent
Deng

(10) Patent No.: US 8,137,370 B2
(45) Date of Patent: Mar. 20, 2012

(54) POWERED SURGICAL HANDPIECE WITH IMPROVED LATCH MECHANISM AND ROTARY TO OSCILLATING OUTPUT DRIVE

(75) Inventor: Wenjie Deng, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 1414 days.

(21) Appl. No.: 11/265,242

(22) Filed: Nov. 2, 2005

(65) Prior Publication Data

US 2007/0100362 A1    May 3, 2007

(51) Int. Cl.
*A61B 17/32* (2006.01)
*A61B 17/00* (2006.01)
(52) U.S. Cl. .......................... 606/169; 606/82
(58) Field of Classification Search ............. 409/200; 475/163, 174; 606/169, 171, 82
See application file for complete search history.

(56) References Cited

U.S. PATENT DOCUMENTS

| | | | | |
|---|---|---|---|---|
| 2,070,281 | A * | 2/1937 | Leggiadro | 606/82 |
| 3,886,805 | A * | 6/1975 | Koderman | 74/52 |
| 4,299,402 | A * | 11/1981 | Hoffman | 279/75 |
| 5,056,268 | A * | 10/1991 | Wolff | 451/357 |
| 5,263,972 | A * | 11/1993 | Evans et al. | 606/176 |
| 5,556,399 | A * | 9/1996 | Huebner | 606/80 |
| 5,871,493 | A | 2/1999 | Sjostrom et al. | |
| 6,312,441 | B1 | 11/2001 | Deng | |
| 7,497,860 | B2 * | 3/2009 | Carusillo et al. | 606/82 |
| 2003/0178794 | A1 * | 9/2003 | Chen et al. | 279/22 |
| 2004/0092991 | A1 | 5/2004 | Deng | |

FOREIGN PATENT DOCUMENTS

WO    WO 9417944 A1 *    8/1994

OTHER PUBLICATIONS

Stryker Instruments, USeries Dura Guards Instructions for Use, May 2004 (8 pages).
Stryker Endoscopy, Bone Plug Handpiece Drawings C-F, prior to Jul., 2005 (7 pages).
Stryker Endoscopy Handpieces pp. 9-12, prior to Jul. 2005 (4 pages).

* cited by examiner

*Primary Examiner* — Thomas C. Barrett
*Assistant Examiner* — David Bates
(74) *Attorney, Agent, or Firm* — Flynn, Thiel, Boutell & Tanis, P.C.

(57) ABSTRACT

A powered surgical handpiece includes a chuck assembly with a chuck having apertures. The chuck assembly is surrounded by a collar having slots on an inner face. The apertures and slots receive balls. In use, the collar is moved axially toward the handpiece against a spring force so that the chuck is viewable. A base tab of a cutting accessory is inserted into the chuck. When the collar is released, detents of the base tab are radially aligned with at least two balls and apertures. When a biasing spring moves the collar outwardly, the respective balls move radially inwardly into the detents to fixedly lock the cutting accessory. The handpiece includes a single eccentric gear shaft that receives a rotary force at one end and moves about an orbital path at a second end. An oscillator receiver of an oscillator receives the barrel. Movement of the barrel about the orbital path results in oscillation of the oscillator about its axis. The oscillator is fixedly secured to the chuck and thus oscillates a cutting accessory mounted therein.

39 Claims, 17 Drawing Sheets

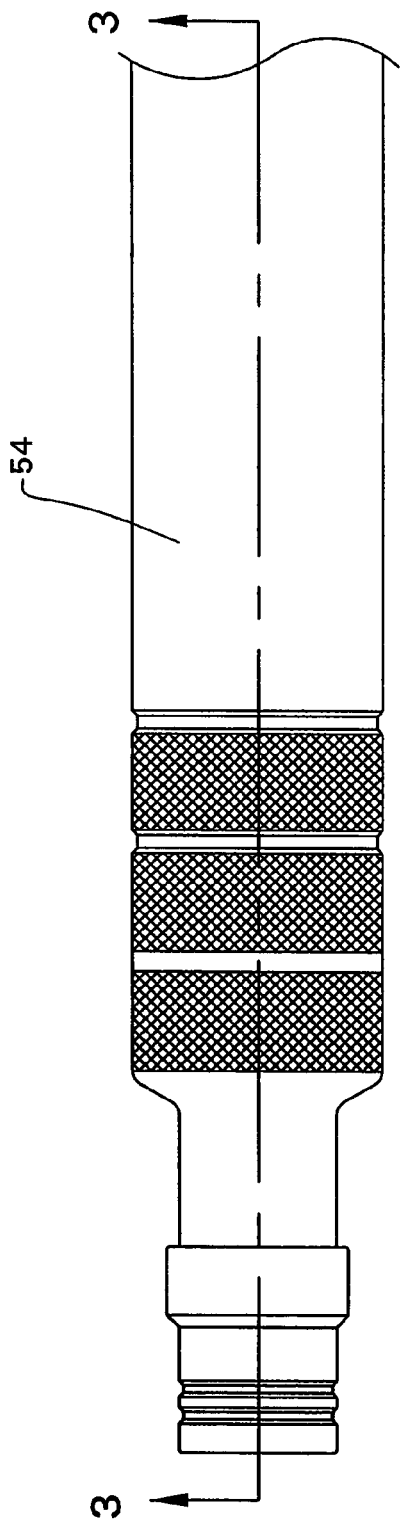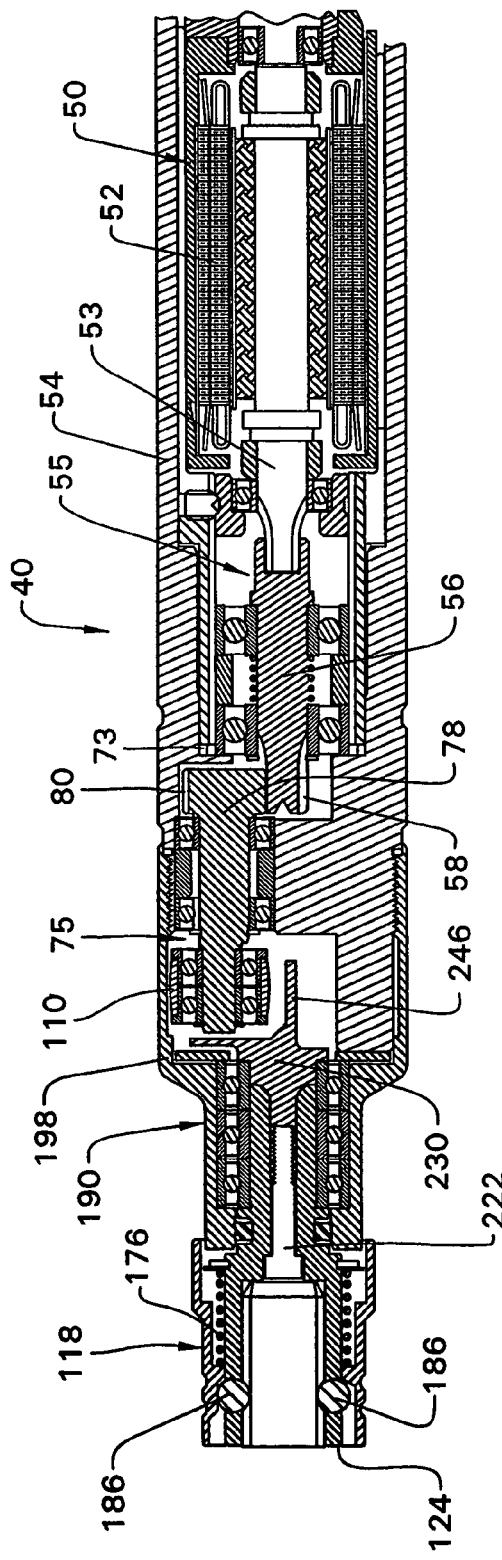

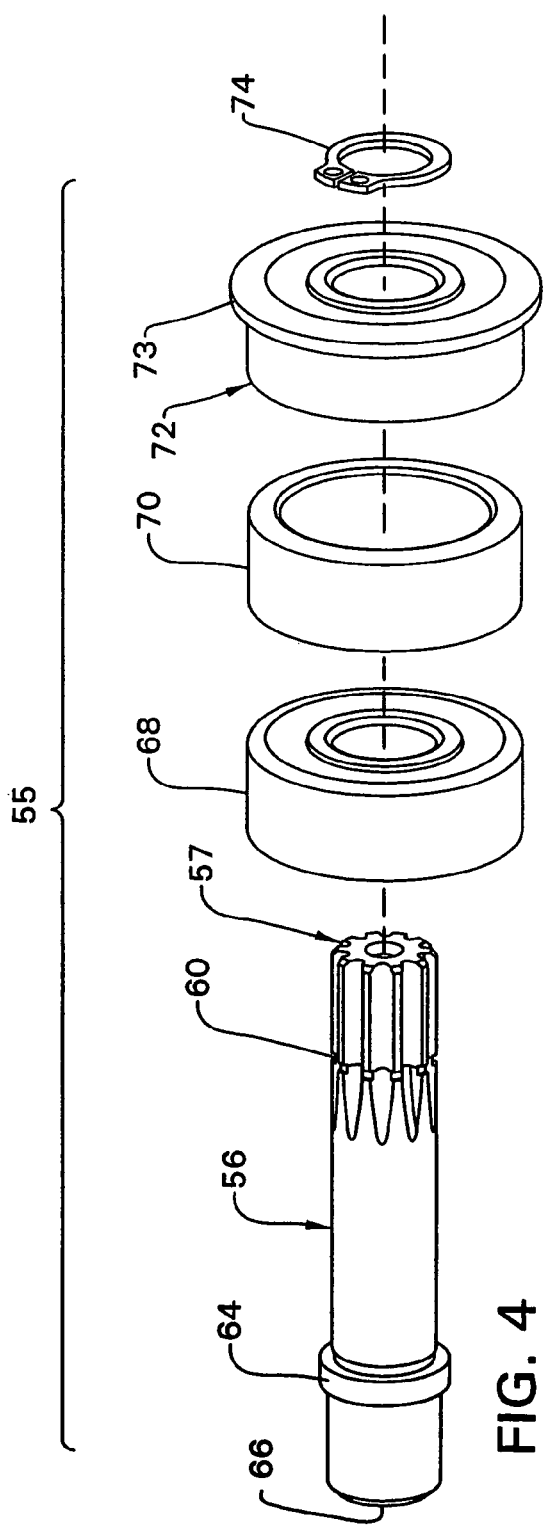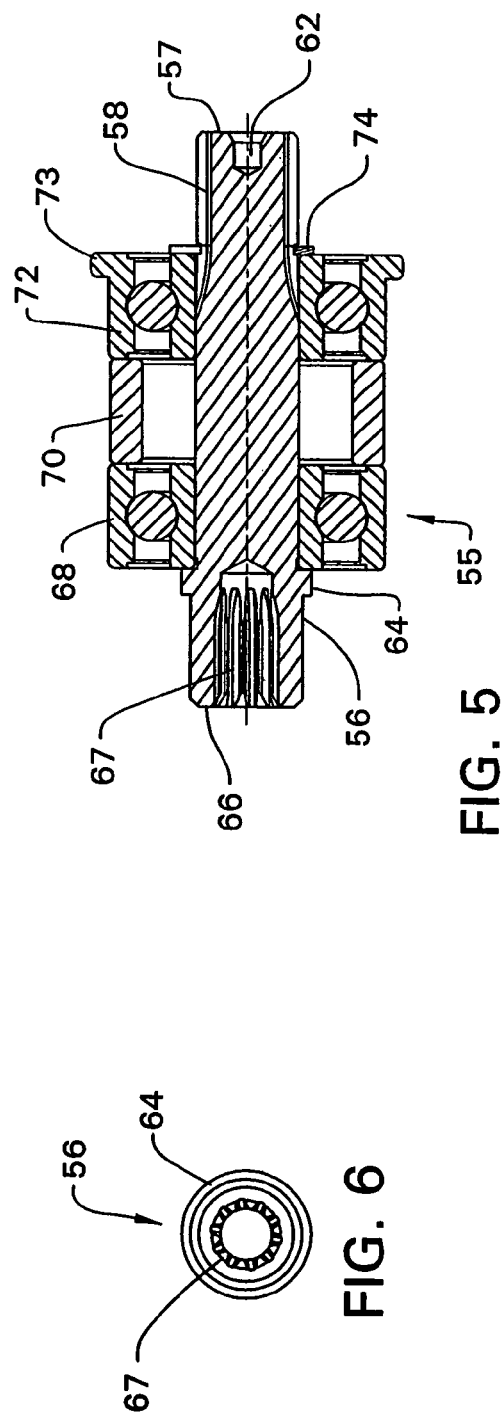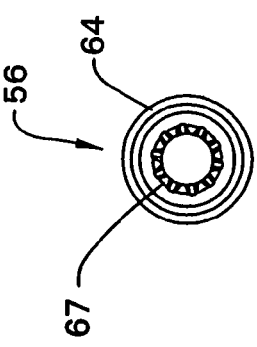
FIG. 4
FIG. 5
FIG. 6

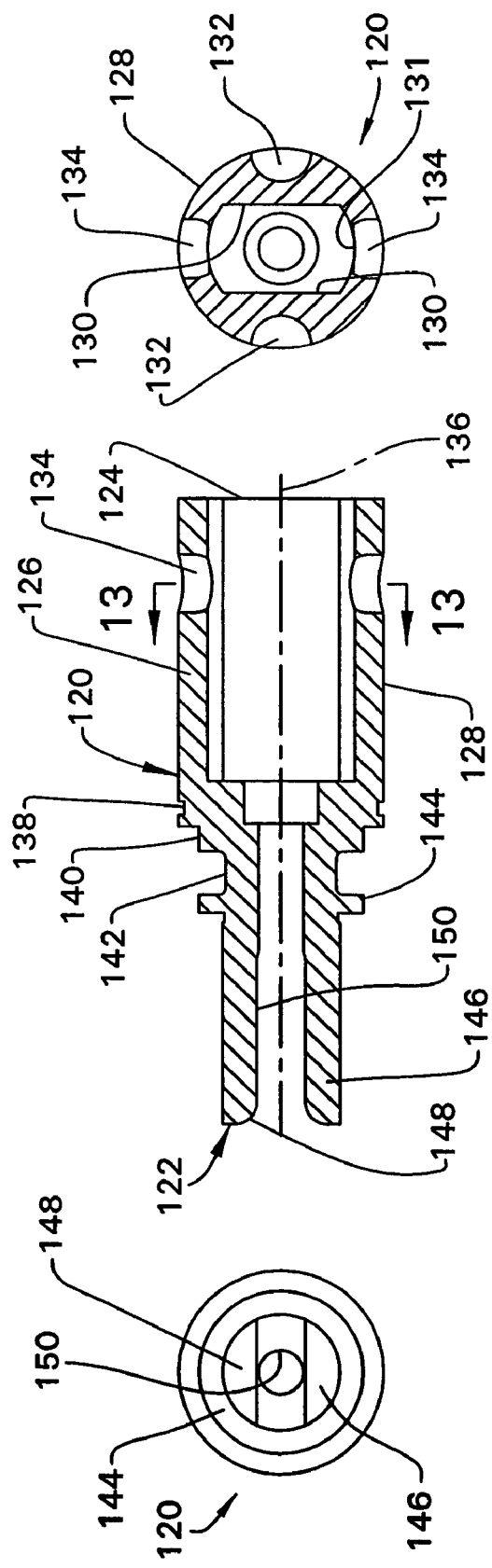

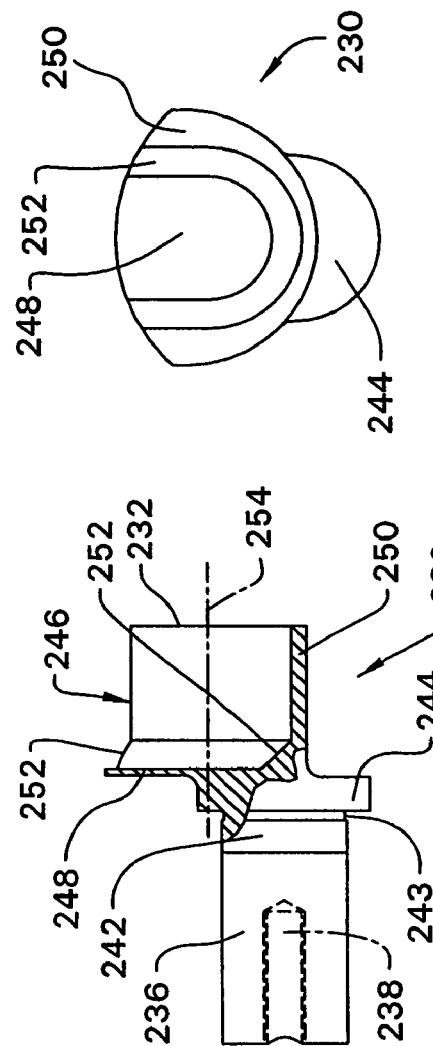
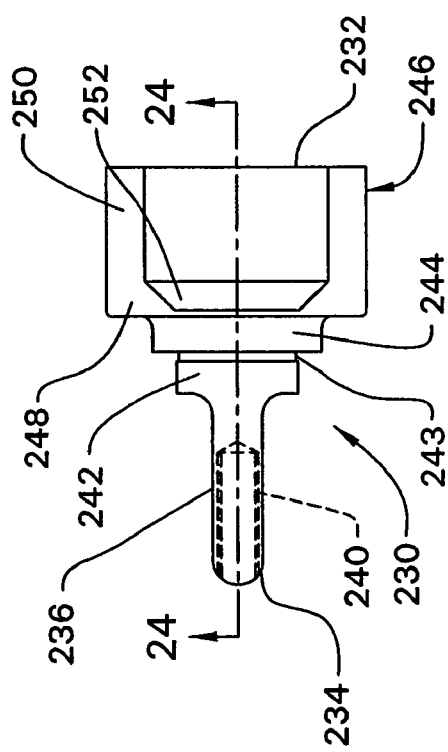
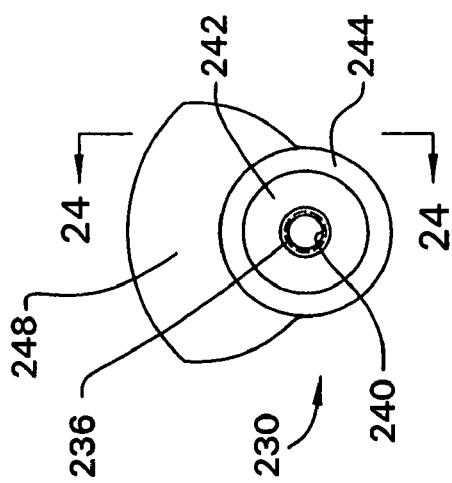

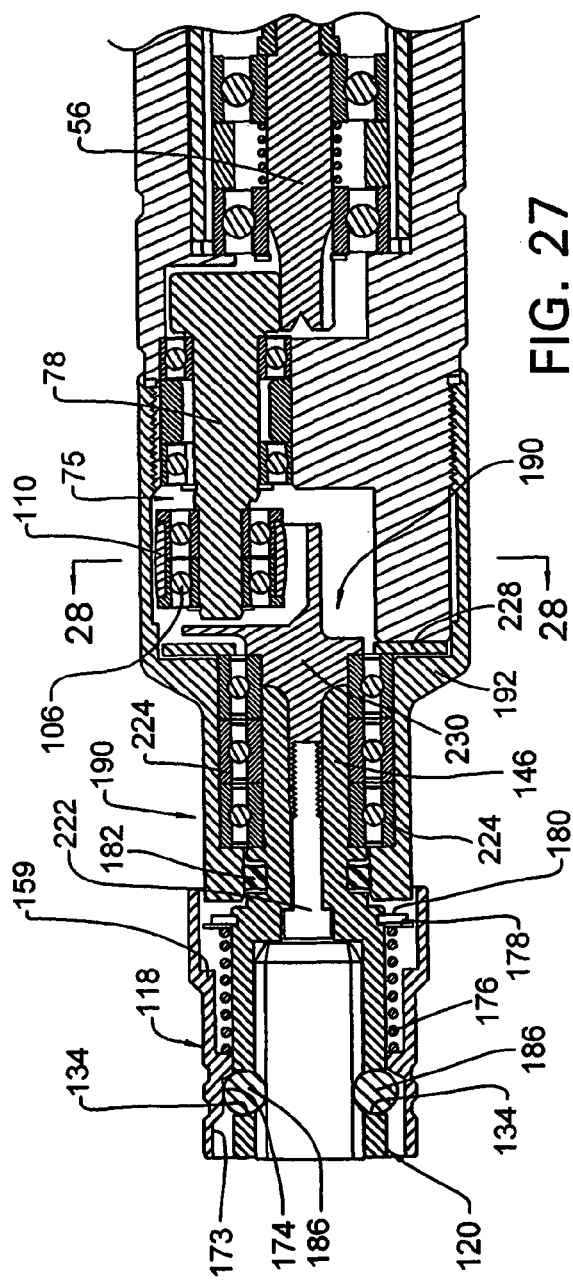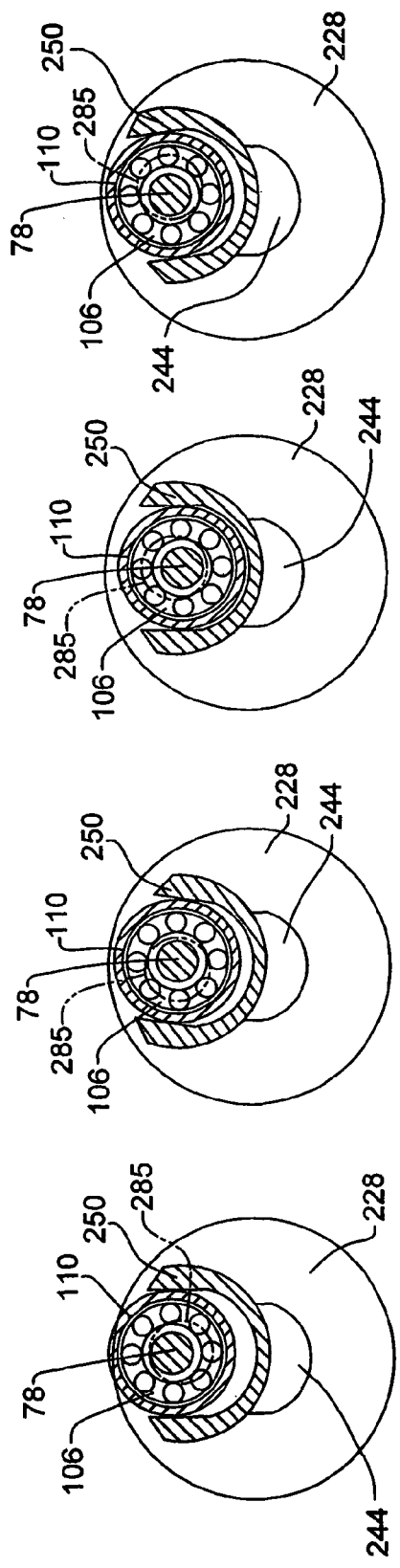

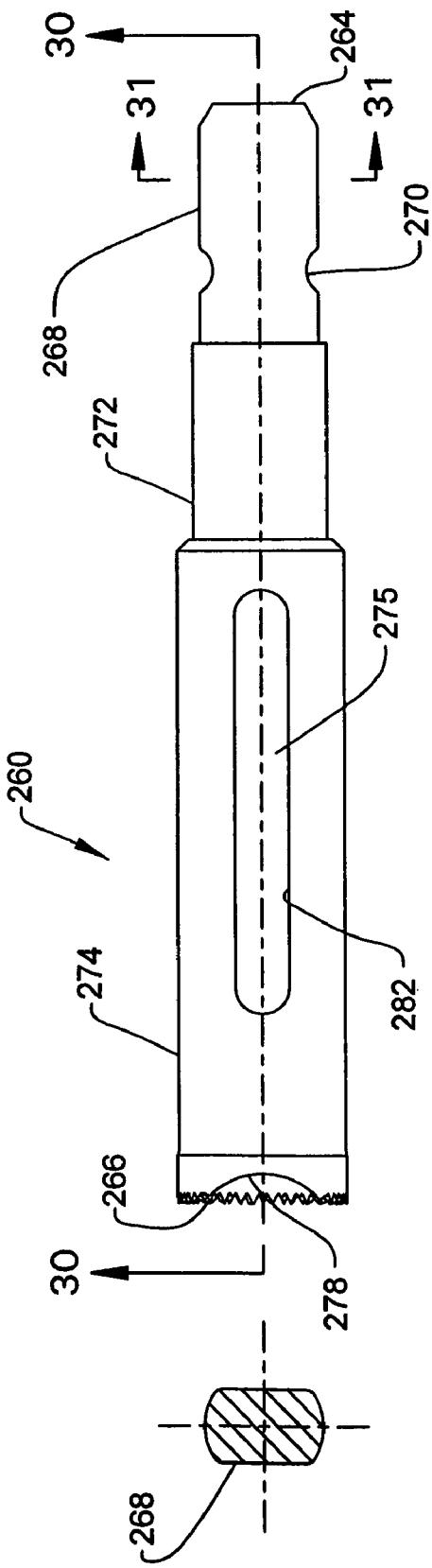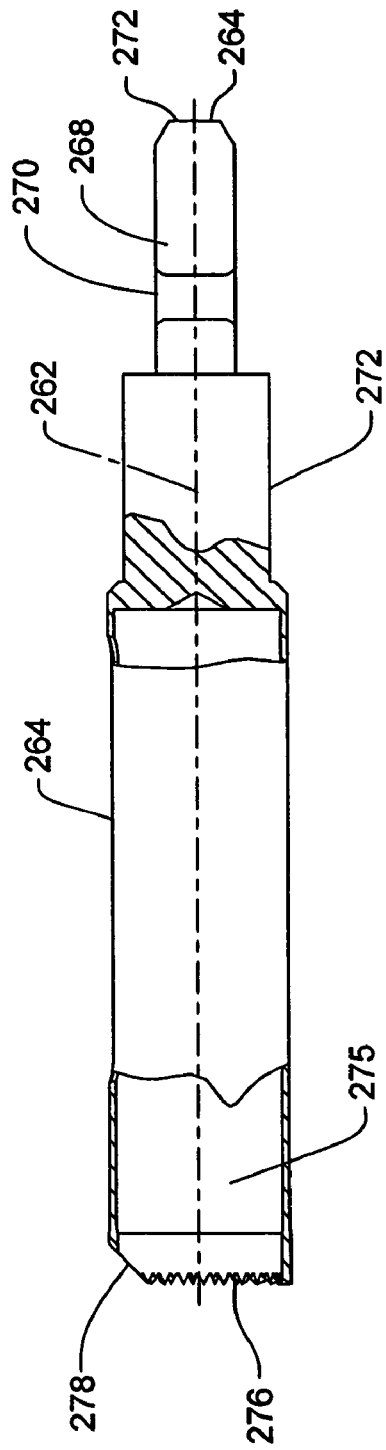
FIG. 29
FIG. 30
FIG. 31

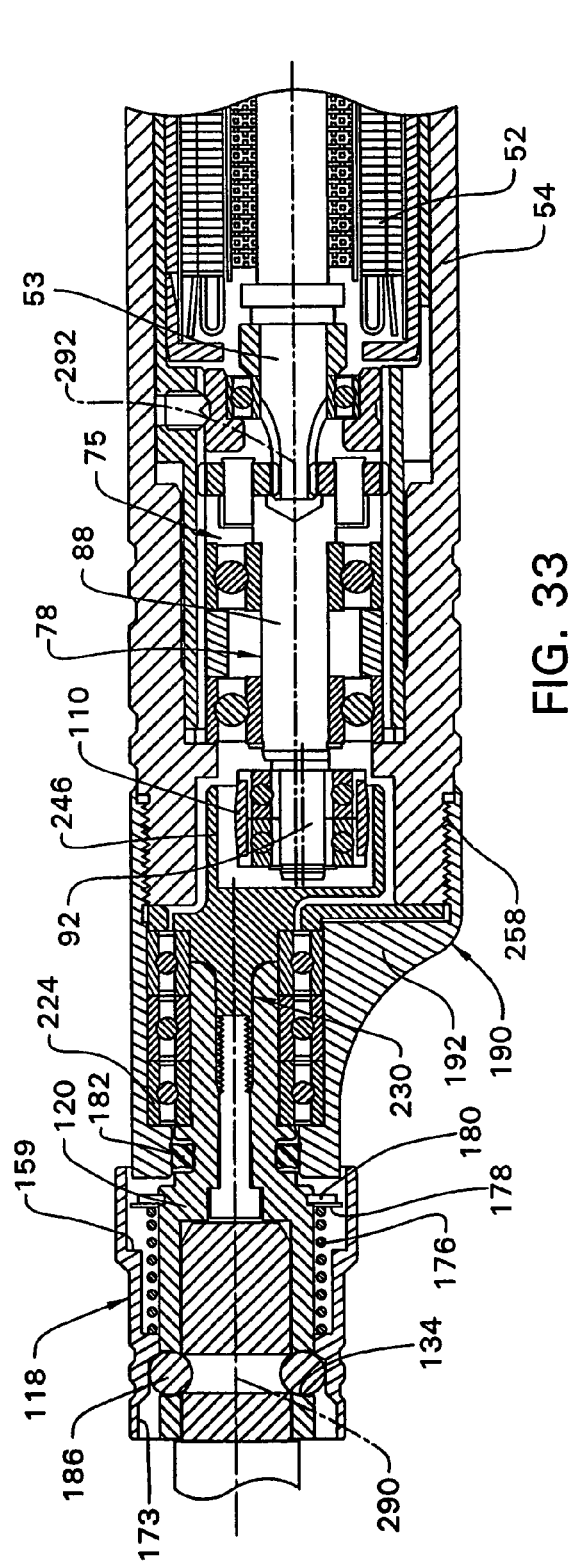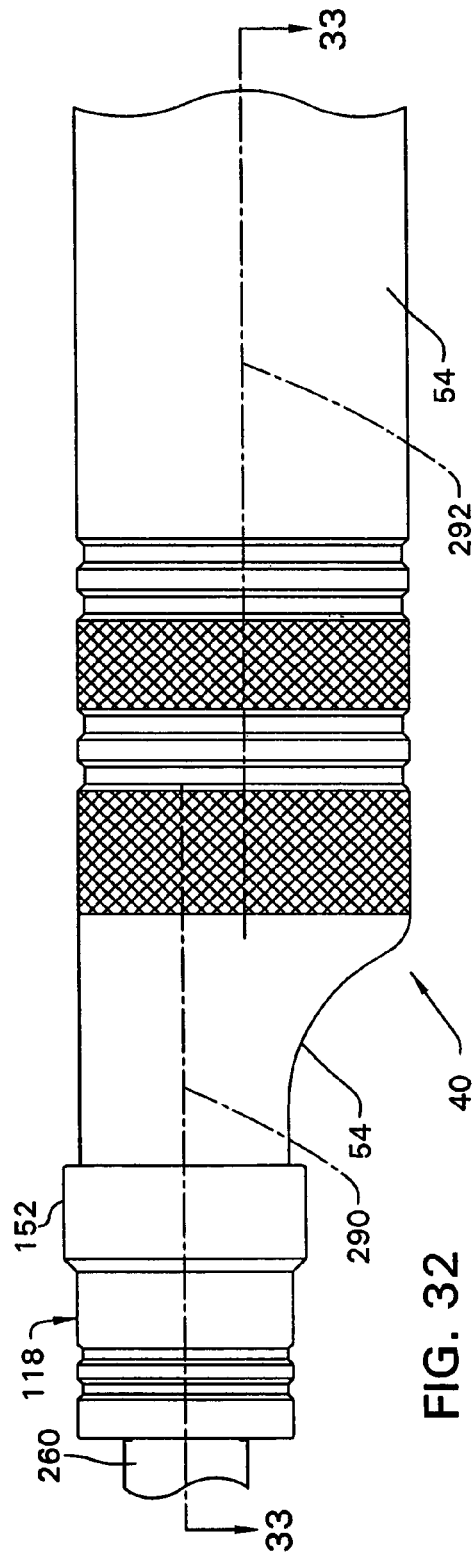
FIG. 33
FIG. 32

POWERED SURGICAL HANDPIECE WITH IMPROVED LATCH MECHANISM AND ROTARY TO OSCILLATING OUTPUT DRIVE

FIELD OF THE INVENTION

This invention generally relates to a surgical handpiece, and more particularly to a surgical handpiece including an improved latch mechanism for fixedly receiving a surgical cutting accessory and an oscillator assembly that receives a rotary output from a gear assembly arrangement to oscillate the surgical cutting accessory.

BACKGROUND OF THE INVENTION

Powered surgical tools are utilized extensively in modern surgery. Typically, these tools include a handpiece which houses a motor. A cutting accessory is secured to the handpiece for accomplishing a specific medical task. Some powered surgical tools are provided with drills or burrs for cutting bores into bone or hard tissue or for selectively removing portions thereof, such as bone graft harvesting. Still other powered surgical tools are provided with cutting accessories such as saw blades for separating large sections of hard tissue. The ability to use powered surgical tools has lessened the physical strain on physicians and other personnel when performing medical procedures on a patient. Moreover, most surgical procedures can be performed more quickly and more accurately with powered surgical tools than with the manual equivalents that preceded them.

In some types of conventional powered surgical tools, the cutting accessory is mounted within an attachment, and the cutting accessory and attachment are then secured to the powered handpiece. Such an arrangement is manufactured by the instant assignee and incorporates therein a ball-detent arrangement for axially positioning a cutting accessory, such as a router. This arrangement includes the cutting accessory having a concave annular groove which cooperates with balls located in the attachment in surrounding relation with the cutting accessory. A collar is provided on the attachment which is manipulated by the user to load and unload the cutting accessory. With this attachment, the collar is set to the "run" position, and the cutting accessory is inserted into the attachment until the balls seat within or "find" the accessory groove. The attachment and cutting accessory are then installed on the handpiece by manipulating a collar provided on the handpiece. The attachment is removed from the handpiece by again manipulating the handpiece collar, and then the cutting accessory is removed from the attachment by setting the attachment collar to the "unlock" position. A disadvantage of this arrangement is that the user must manually manipulate two collars during assembly. That is, one collar must be used to lock the attachment to the handpiece, and another collar must be used to position the cutting accessory relative to the attachment.

Another type of conventional powered handpiece manufactured by the assignee is a bone cutter saw chuck assembly including a receptacle for receiving a cutting accessory and a set screw. A screw driver is utilized to rotate the set screw to fixedly mount the cutting accessory in the receptacle. While this arrangement works reasonably well for its intended purpose, the set screw, being a separate component from the chuck assembly, can be lost. Further, the user must remember to sterilize the screw driver in addition to the other components.

Further, the conventional powered handpiece has a single motor that includes a bronze bushing as a rotary bearing and a pair of eccentric output drivers with roller bearings. The motor rotationally drives first ends of the drivers. Second ends of the output drivers are received in a channel of an oscillator. The ends of the eccentric output drivers move about a path and, in combination, pivotally oscillate the oscillator about an axis. The oscillator then oscillates a bone plug cutter located in a chuck to provide a bone cutting operation.

The use of two eccentric output drivers with roller bearings in the handpiece can create heat, and thus wear, which may lead to more frequent repair and/or replacement costs.

In order to address the above problems, or at least minimize the above shortcomings of the known arrangements, a chuck assembly is provided having a collar that is movable against a spring force to enable access to the chuck by a cutting accessory, and which collar is releasable to lock the cutting accessory in the chuck. Further, the handpiece includes a single output driver arrangement, which utilizes an eccentric rotary shaft to provide an oscillating motion for the cutting accessory.

SUMMARY OF THE INVENTION

In the arrangement according to the invention, the handpiece includes a chuck assembly with a chuck having apertures and a collar having slots corresponding to the apertures. Balls are maintained in the apertures by the collar. A spring biases the collar axially outwardly. Moving the collar inwardly compresses the spring, and enables insertion of a cutting accessory into the chuck. Releasing the collar locks the cutting accessory in the chuck.

Further, in the arrangement of the invention the output drive of the handpiece includes a single eccentric output shaft in the housing. Rotation of the eccentric output shaft moves one end thereof about an orbital path. The end coacts with an oscillator assembly having an oscillator output shaft. The orbital movement of the end of the eccentric output shaft causes back and forth pivoting or oscillating of the oscillator output shaft about its longitudinal axis. The oscillating movement is transferred to a cutting accessory. Ball bearings at the end of the single eccentric output shaft reduce heat generated by operation of the handpiece. Providing a single output shaft reduces the production cost and also the number of parts requiring possible repair in the handpiece.

BRIEF DESCRIPTION OF THE DRAWINGS

FIG. 2 is an enlarged, perspective and fragmentary side view of the central and distal parts of the handpiece apparatus of FIG. 1;

FIG. 3 is an enlarged longitudinal cross-sectional view taken generally along line 3-3 in FIG. 2;

FIG. 4 is an enlarged, partially exploded perspective view of the extension gear assembly of the handpiece apparatus;

FIG. 5 is an enlarged, longitudinal cross-sectional view of the extension gear assembly of FIG. 4;

FIG. 6 is an enlarged front view the extension gear shaft shown in FIG. 4;

FIG. 12 is an enlarged, longitudinal cross-sectional view of the chuck taken generally along line 12-12 in FIG. 11;

FIG. 13 is a cross-sectional view of the chuck taken generally along line 13-13 in FIG. 12;

FIG. 14 is an enlarged end view of the chuck shown in FIG. 11;

FIG. 22 is an enlarged side view of the oscillator shown in FIG. 20;

FIG. 23 is an enlarged end view of the oscillator shown in FIG. 22;

FIG. 24 is a longitudinal cross-sectional view of the oscillator taken generally along line 24-24 in FIG. 23;

FIG. 25 is an enlarged end view of the oscillator taken at the end opposite to the end view illustrated in FIG. 23;

FIG. 27 is an enlarged, longitudinal cross-sectional and fragmentary view of the distal part of the handpiece apparatus illustrated in FIG. 1;

FIGS. 28A-28D are enlarged, partial cross-sectional views of the handpiece apparatus taken generally along line 28-28 in FIG. 27, showing the orbital path about a fixed circle of the barrel within the barrel receiver of the oscillator, wherein the housing is not illustrated for purposes of simplicity;

FIG. 29 is an enlarged, side view of a cutting accessory for use with the handpiece apparatus;

FIG. 30 is an enlarged longitudinal and partially cross-sectional side view of the cutting accessory taken generally along line 30-30 of FIG. 29;

FIG. 31 is an enlarged cross-sectional view of the cutting accessory taken generally along line 31-31 of FIG. 29;

FIG. 32 is an enlarged, perspective and fragmentary side view of the central and distal parts of a second embodiment of the handpiece apparatus and part of the cutting accessory; and FIG. 33 is a longitudinal cross-sectional view of the handpiece apparatus taken generally along line 33-33 of FIG. 32.

Figure 1:
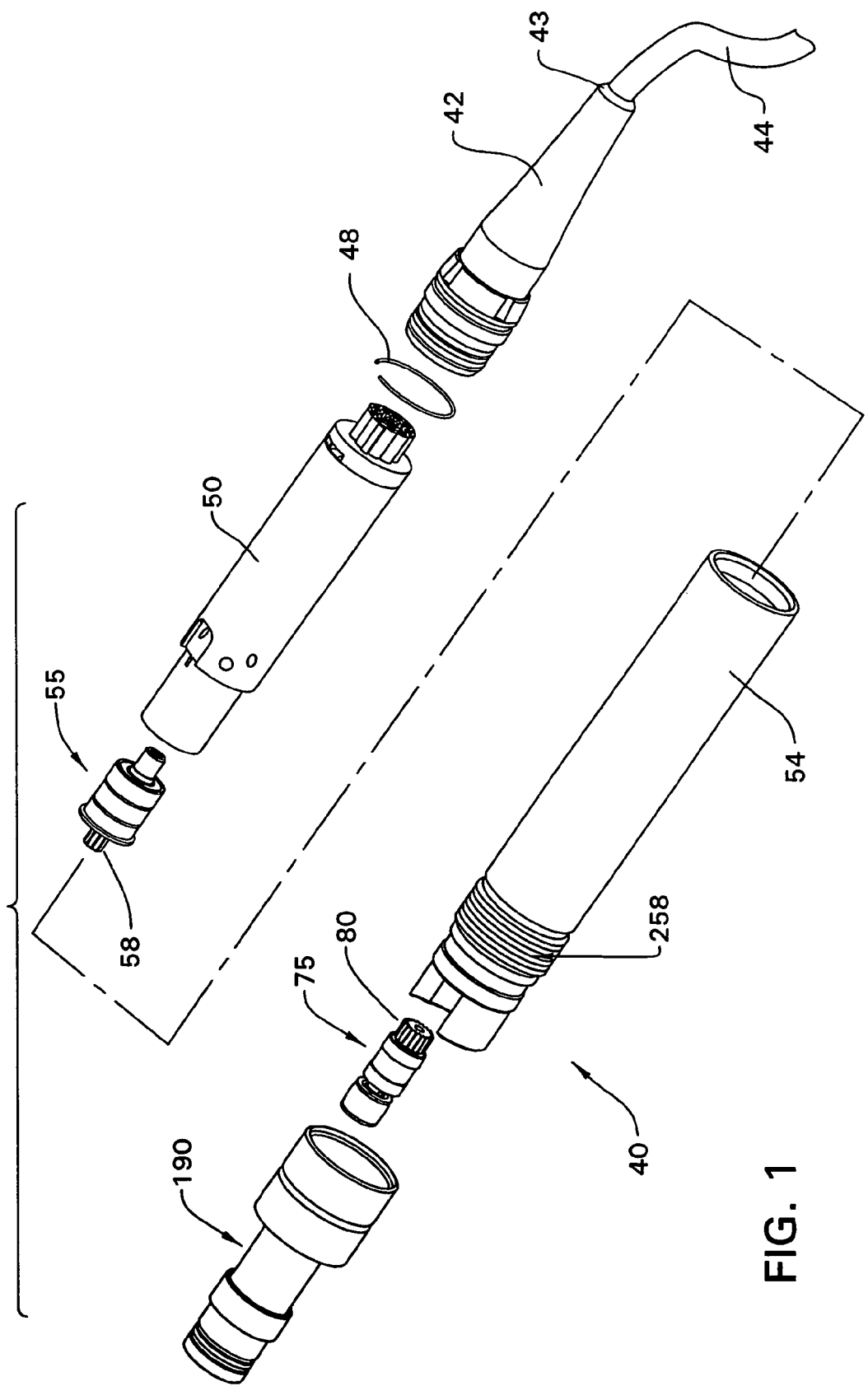
FIG. 1 is a partially exploded perspective and fragmentary view of the handpiece apparatus according to the invention.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the tool arrangement and designated parts thereof. The words "forwardly" and "distally" will refer to the direction toward the end of the tool arrangement which is closest to the patient, and the words "rearwardly" and "proximally" will refer to the direction away from the end of the tool arrangement which is furthest from the patient. Said terminology will include the words specifically mentioned, derivatives thereof, and words of similar import.

DETAILED DESCRIPTION

FIGS. 1-3 illustrate a first handpiece apparatus 40 according to the invention. In the illustrated embodiment, a cable assembly piece 42 at a proximal end 43 of the apparatus receives a cable 44 therein. The handpiece apparatus 40 includes a retaining wire or clip 48 located between the cable assembly piece 42 and a cutter power assembly, such as cutter motor assembly 50.

Motor Assembly

The motor assembly 50 is provided with power from the cable 44. As shown in FIG. 3, the cutter motor assembly 50 includes stator coils 52 and a motor output shaft 53 that provides a rotary output. The cutter motor assembly 50 is well known, and thus the structure and operation thereof are not described in detail herein. In some embodiments, instead of cable 44, a battery may be utilized to provide power to the stator coils 52. Other convenient types of motive power sources, such as a pneumatic motor, may also be utilized. The motor assembly 50 is supported in a housing 54 in a conventional manner, and thus the support structure is not described in detail herein.

Extension Gear Assembly

As illustrated in FIG. 3, the handpiece apparatus 40 further includes an extension gear assembly 55 that is rotatably coupled with the motor output shaft 53 of the cutter motor assembly 50. Other types of coupling arrangements are also contemplated.

The extension gear assembly 55 illustrated in FIGS. 4 and 5 includes a generally cylindrical extension gear shaft 56 having a first distal end 57 defining thereon gear teeth 58 which project radially outwardly and extend axially along shaft 56. A slot 60 extends transversely to the gear teeth 58 and extends about the circumference of the gear shaft 56. The first distal end 57 also includes an axially oriented blind bore or aperture 62. The extension gear shaft 56 includes a stepped cylindrical portion or shoulder 64 positioned toward a second proximal end 66 of the gear shaft. The second proximal end 66 of the extension gear shaft 56 includes an axially oriented blind bore defined by an array of inwardly projecting gear teeth 67 as illustrated in FIGS. 5 and 6.

The extension gear assembly 55 shown in FIG. 4 includes the extension gear shaft 56, an annular bearing, such as ball bearing 68, a spacer ring 70, and a flanged annular bearing, such as flanged ball bearing 72 including a radially projecting flange part 73 and a retaining ring 74. The bearing 68, spacer ring 70 and flanged bearing 72 are assembled onto the gear shaft 56 as shown in FIG. 5. The bearing 68 abouts against the stepped cylinder portion 64. The retaining ring 74 is secured in the slot 60 to axially lock the elements onto the extension gear shaft 56.

Eccentric Output Assembly

Figure 7:
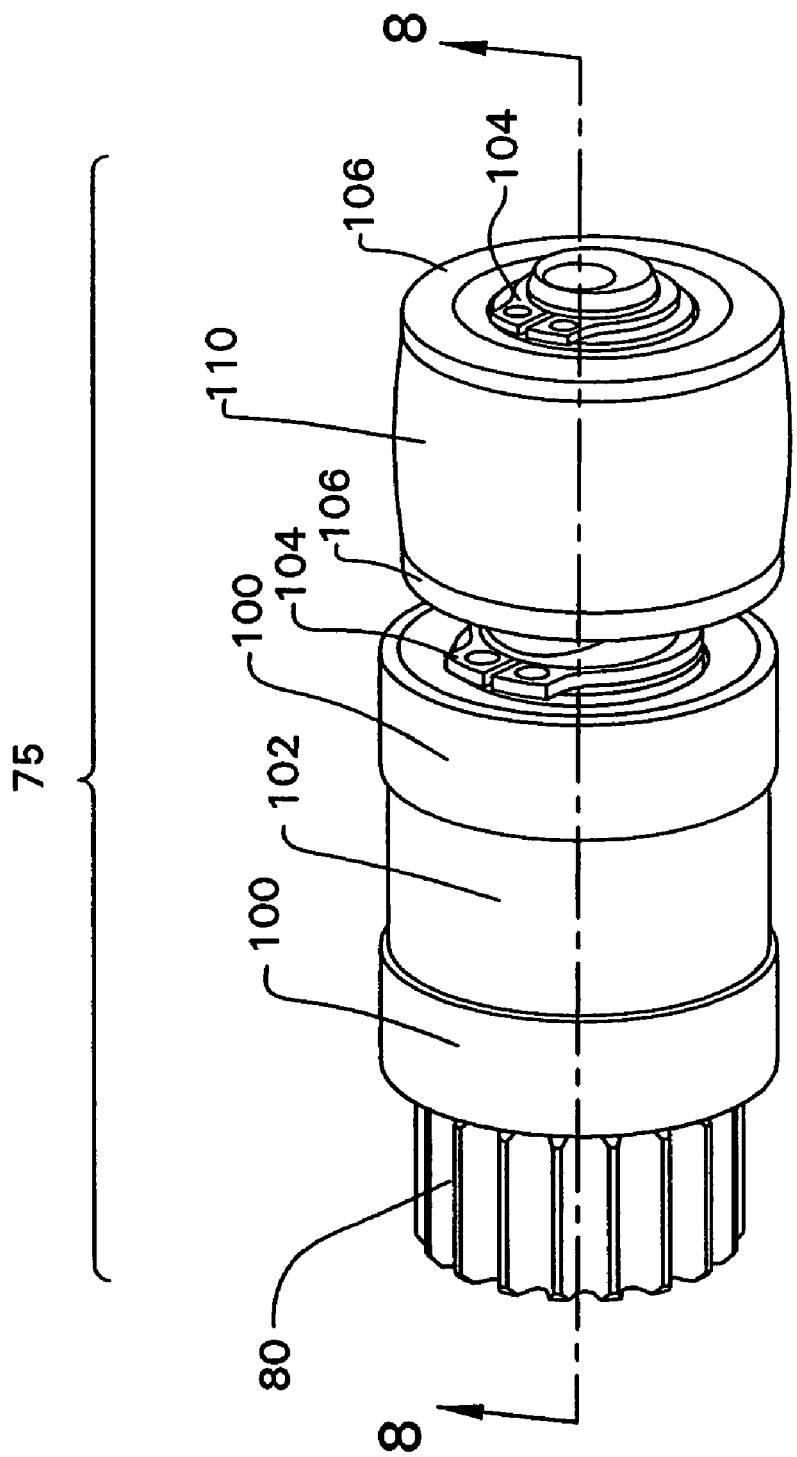
FIG. 7 is an enlarged, perspective view of the eccentric gear shaft assembly.
Figure 8:
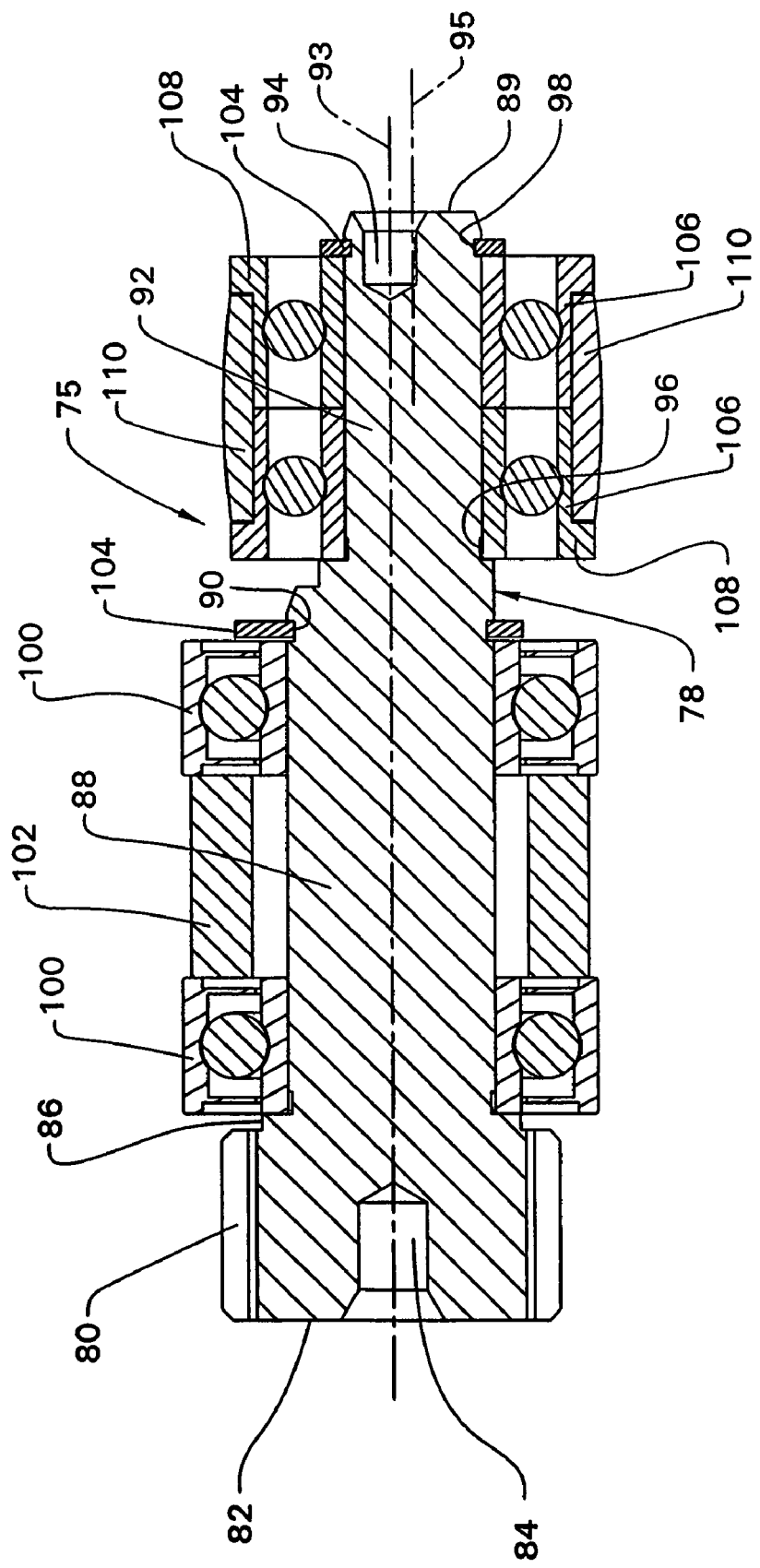
FIG. 8 is an enlarged longitudinal cross-sectional view of the eccentric gear shaft assembly taken generally along line 8-8 in FIG. 7.

The handpiece apparatus 40 includes a linking assembly, for example an eccentric output assembly comprising an eccentric gear assembly 75 illustrated in FIGS. 7 and 8. As shown in FIG. 8, the eccentric gear assembly 75 includes a single eccentric gear shaft 78. The eccentric gear shaft 78 includes a plurality of radially outwardly directed teeth 80 at a first proximal end 82 thereof. The first proximal end 82 of the eccentric gear shaft 78 includes a blind proximal aperture or bore 84 oriented along the longitudinal axis thereof for tooling purposes. As illustrated in FIG. 8, the eccentric gear shaft 78 includes a stepped end portion 86 supporting the teeth 80 and a central cylindrical portion 88 having a diameter less than the diameter of the stepped end portion 86. Toward a distal end 89 of the eccentric gear shaft 78, the central portion 88 includes a radially inwardly projecting slot 90 extending about the circumference thereof. The distal end 89 of the eccentric gear shaft 78 includes an eccentric shaft portion 92. The eccentric shaft portion 92 includes an offset blind aperture 94 for tooling purposes that is oriented substantially in alignment with a longitudinal axis 93 of the central portion 88 and bore 84, but is offset from and generally parallel to a longitudinal axis 95 of the eccentric shaft portion 92. The eccentric shaft portion 92 also includes a radially inwardly projecting slot 96 near the central portion thereof that extends about the circumference thereof, and a radially inwardly projecting slot 98 near the distal end 89 that extends about the circumference of the eccentric shaft portion 92.

The assembled eccentric gear assembly 75 includes a first annular bearing 100 that mounts on the central cylindrical portion 88 and axially abuts the stepped end portion 86 of the gear shaft 78. An annular spacer 102 is located on the eccentric gear shaft 78 with a first side abutting the bearing 100. A second annular bearing 100 is located on the central cylindrical portion 88 abutting a second side of the spacer 102. A retaining ring 104 mounts into the slot 90 at the distal end of the central portion 88 of the eccentric gear shaft 78 to axially fix or maintain the bearings 100 and spacer 102 on the central portion.

As shown in FIGS. 7 and 8, the eccentric gear assembly 75 includes flanged bearings which in the illustrated embodiment define a two-part component including the first and second annular ball bearings 106 positioned axially adjacent one another. Ball bearings 106 have inner diameters dimensioned for mounting over the eccentric shaft portion 92. One side of a first flanged bearing 106 abuts against the central portion 88 of the gear shaft 78 with a radially projecting annular flange 108 oriented toward the central portion.

Figure 9:
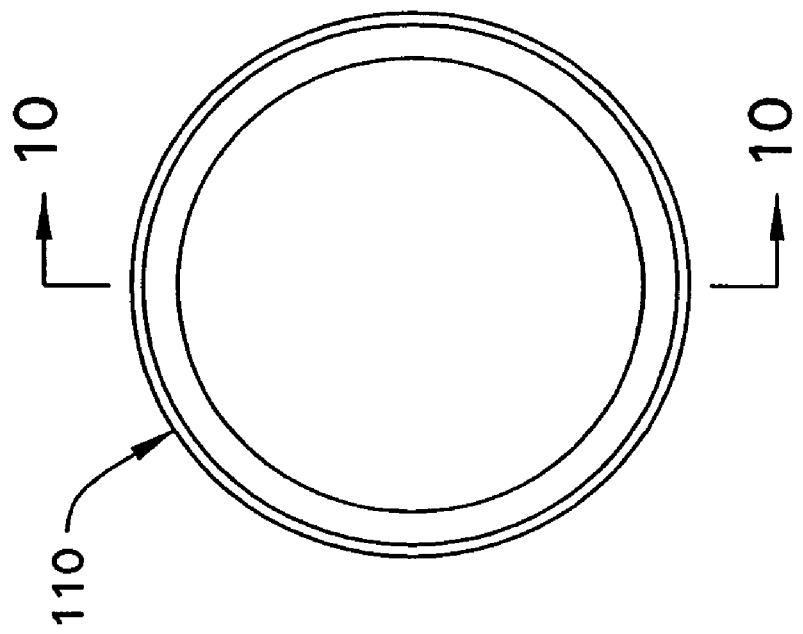
FIG. 9 is an enlarged end view of the barrel shown in FIG. 7.
Figure 10:
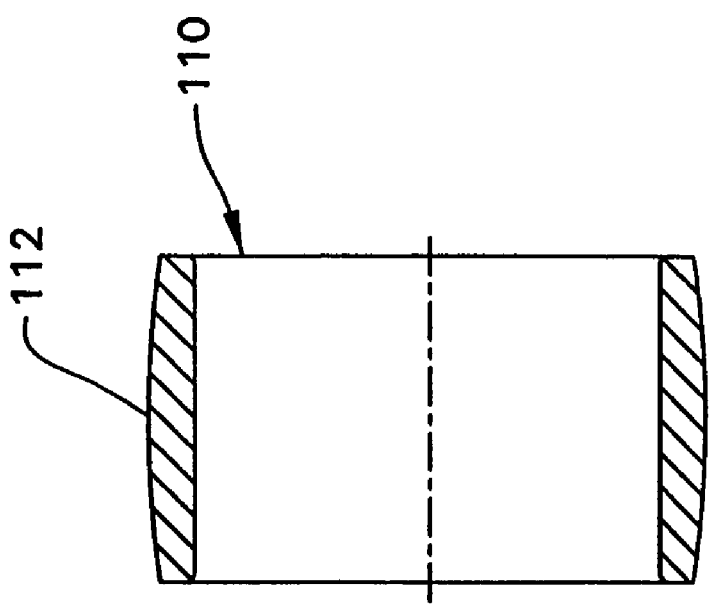
FIG. 10 is an enlarged, cross-sectional view of the barrel taken generally along line 10-10 in FIG. 9.

The eccentric gear assembly 75 further includes a transfer member and preferably a single generally cylindrical hollow barrel or a single barrel member 110 as shown in FIGS. 9 and 10. The single barrel 110 may have a cylindrical shape, but in the illustrated embodiment, the preferred barrel 110 has a slightly convex radially outwardly oriented surface 112. The inner diameter of the barrel 110 is substantially the same as the outer diameter of the flanged bearings 106. Thus, the barrel 110 mounts onto the eccentric shaft portion 92 with each end abutting one of the radial flanges 108 of the flanged bearings 106. As shown in FIG. 8, the second flanged bearing 106 is positioned on the eccentric shaft portion 92 and received within the barrel 110, except for the radially projecting flange 108 which abuts a second end of the barrel 110. A second retaining ring 104 secured in slot 98 then limits axial movement of the bearings 106 and the barrel 110 positioned thereon.

Chuck Subassembly

Figure 11:
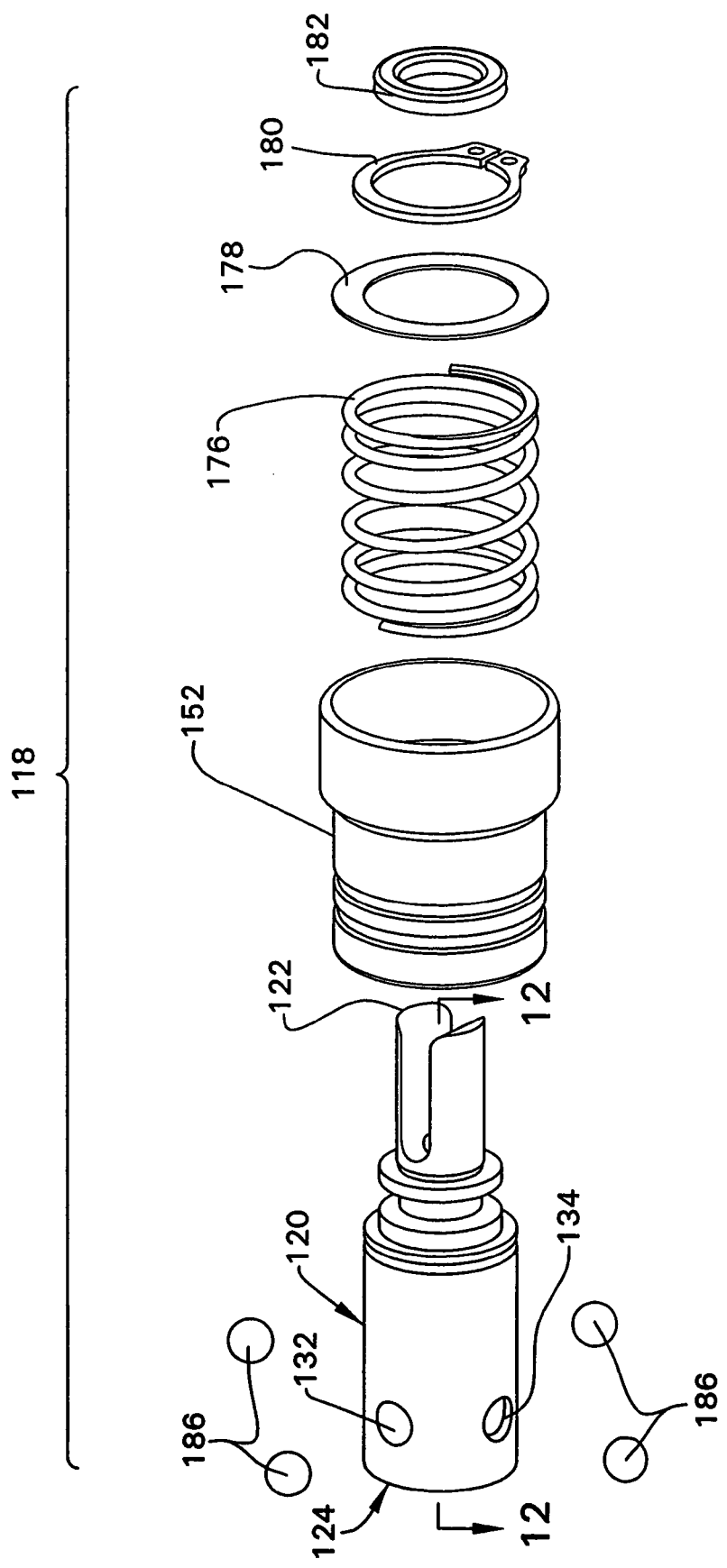
FIG. 11 is an enlarged, exploded perspective view of the chuck subassembly of the oscillator assembly.

The chuck subassembly 118 shown in FIG. 11 includes a chuck 120 with a proximal end 122 and a distal receiving end 124. As shown in FIG. 12, at the distal receiving end 124, the chuck 120 has a generally tubular receiving part 126 with a cylindrical outer face 128. As shown in FIG. 13, the receiving part 126 includes a hollow and substantially rectangular inner chamber defined by a pair of facing side walls 130 and a pair of rounded end walls 131.

As shown in FIG. 13, the outer face 128 of the receiving part 126 has a pair of sidewardly opening bores 132 and a pair of bores 134 that extend into and communicate with the inner chamber. The apertures 132, 134 are spaced equidistantly and alternatingly about the outer face 128 of the receiving part 126. As shown in FIG. 12, the bores 132, 134 are all aligned radially with a longitudinal axis 136 of the chuck 120.

The chuck 120 includes a radially inwardly projecting slot 138 extending about the circumference of the outer face 128 and located proximally from the apertures 132, 134. The chuck 120 includes a first lower step part 140 integral with the receiving part 126. A second lower step part 142 integral with the step part 140 has a diameter less than the diameter of the step part 140. A further step 144 of the chuck 120 is located axially adjacent and is integral with the second step part 142. Step 144 has a diameter which is substantially the same as the diameter of step part 140. Finally, the chuck 120 includes a pair of prongs 146 that extend axially outwardly from step 144. The prongs 146 are integral with step 144, and rounded tips 148 of the prongs 146 define the proximal end 122 of the chuck 120.

FIG. 14 is an end view as seen along the longitudinal axis 136 of the chuck 120 that shows a centrally located, proximally opening screw receiving aperture 150 extending longitudinally through chuck 120.

Figure 15:
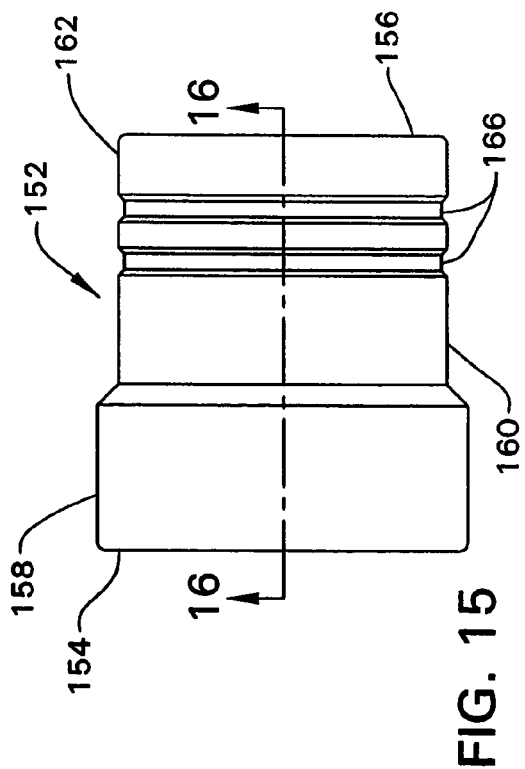
FIG. 15 is an enlarged side view of the collar of the chuck subassembly illustrated in FIG. 11.

The chuck subassembly 118 shown in FIG. 11 includes an annular collar 152 for surrounding the chuck 120. The collar 152 illustrated in FIGS. 15-17 has a proximal end 154 and a distal end 156. The proximal end includes a proximal end tubular collar portion 158 having a greater diameter than a centrally located and inwardly stepped tubular collar portion 160. A step shoulder 159 located where the portions 158, 160 are joined, faces the proximal end. A distal end collar portion 162 has an inwardly projecting stepped part 164 located axially adjacent the tubular collar portion 160. A pair of radially inwardly projecting annular channels 166 each extend about an exterior surface of the distal end collar portion 162 of the collar 152. Channels 166 are axially spaced from one another along collar portion 162.

Figure 17:
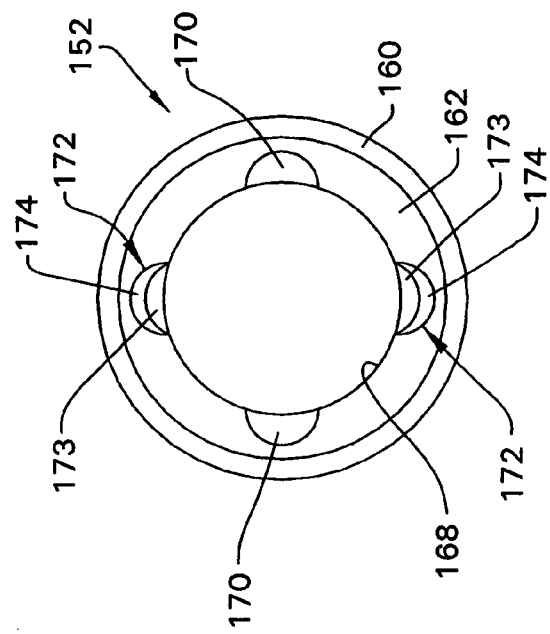
FIG. 17 is an enlarged front end view of the collar illustrated in FIG. 15.

As shown in FIG. 17, an inner annular face 168 of the distal end collar portion 162 includes a first pair of inwardly opening slots 170 extending from the distal end 156 of the collar 152 axially toward the stepped part 164 of the distal end collar portion 162. The closed ends of the apertures or slots 170 are oriented toward the central tubular collar portion 160 and each define a tapered slot end (not shown) for retaining a metal ball.

Figure 16:
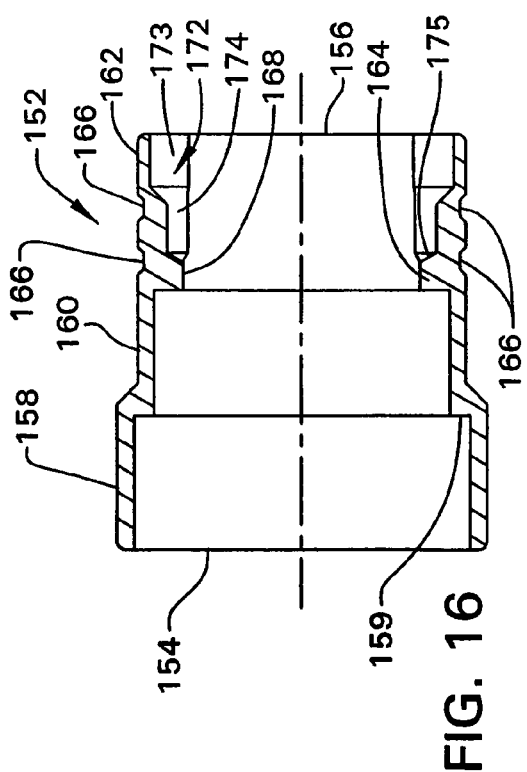
FIG. 16 is an enlarged, cross-sectional view of the collar taken generally along line 16-16 in FIG. 15.

The distal end collar portion 162 further includes a second pair of closed apertures or slots 172 projecting from the distal end 156 of the collar 152 axially inwardly along the inner face 168. As illustrated in FIG. 16, the second pair of slots 172 each include a first slot portion 173 at the distal end 156 and a second stepped slot portion 174. The first slot portion 173 has a greater diameter than the second stepped slot portion 174. The stepped slot portion 174 includes a tapered slot end 175.

The slots 170, 172 have substantially the same length in the axial direction and are spaced equidistantly and alternatingly about the inner face 168 of the chuck 126. The slots 170 are in opposed or facing relationship with one another, as are the slots 172.

Figure 19:
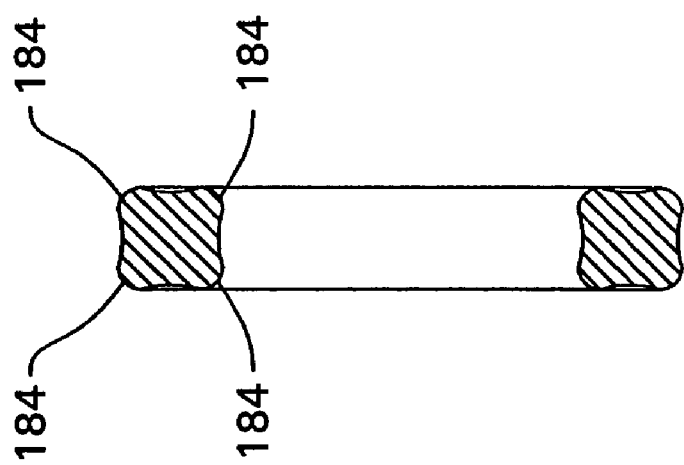
FIG. 19 is an enlarged, cross-sectional view of the quad seal taken generally along line 19-19 in FIG. 18.
Figure 18:
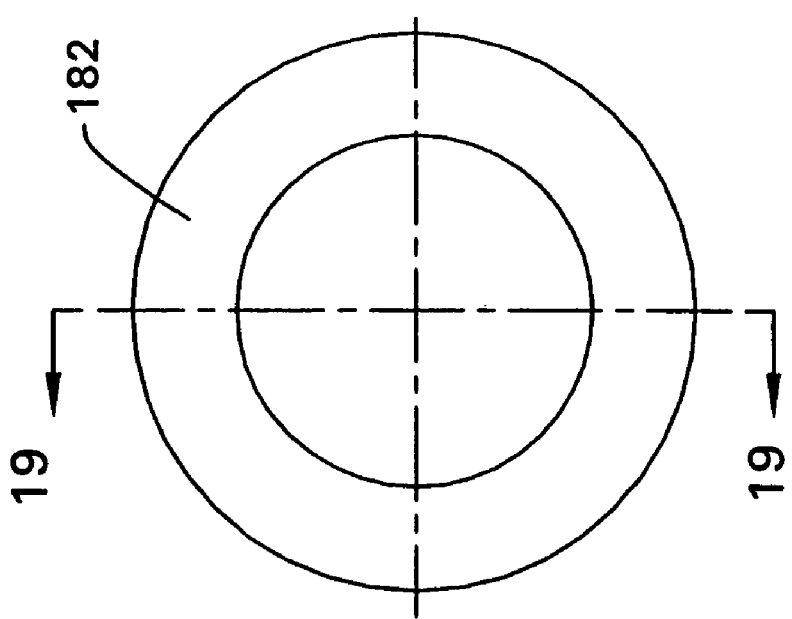
FIG. 18 is an enlarged end view of the quad seal illustrated in FIG. 11.

Returning to FIG. 11, the chuck subassembly further includes a coiled spring 176, an annular washer 178, an annular retainer 180 and an annular quad seal 182. The coiled spring 176 has a substantially constant radius about an axis therealong. The quad seal 182 illustrated in FIGS. 18 and 19 has a substantially rectangular cross-section with four slightly radially and axially outwardly projecting edges 184. Metal balls 186 are provided for seating in the apertures 132, 134, of chuck 120 as shown in FIG. 11.

One method of assembling the chuck subassembly 118 is as follows. First, the balls 186 are inserted into the apertures 132, 134 of the chuck 120. The chuck 120 is axially moved into the collar 152. The coil spring 176 is axially inserted into the proximal end 154 of collar 152 so that a first end of the coil spring bears against a proximally facing surface of the stepped part 164 of the collar 152. The washer 178 shown in FIG. 11 is then used to compress the spring 176. The retainer 180 is seated in slot 138 on the outer face of the chuck 120 to maintain the washer 178 in place against the compressive force of the coil spring 176. Thus the balls 186 and the retainer 180 coact to resist the forces of coil spring 176 and maintain the collar 152 with the chuck subassembly 118. The quad seal 182 is then assembled over the prongs 146 and moved axially therealong and seated in the second lower step part 142 of the chuck 120. The assembled chuck subassembly 118 is illustrated in FIG. 3. In the assembled state, the chuck 120 must be physically maintained in the collar 152 so that the force applied by the coil spring 176 will not move the chuck 120 axially outwardly from the distal end 156 of the collar 152.

Oscillator Assembly

Figure 20:
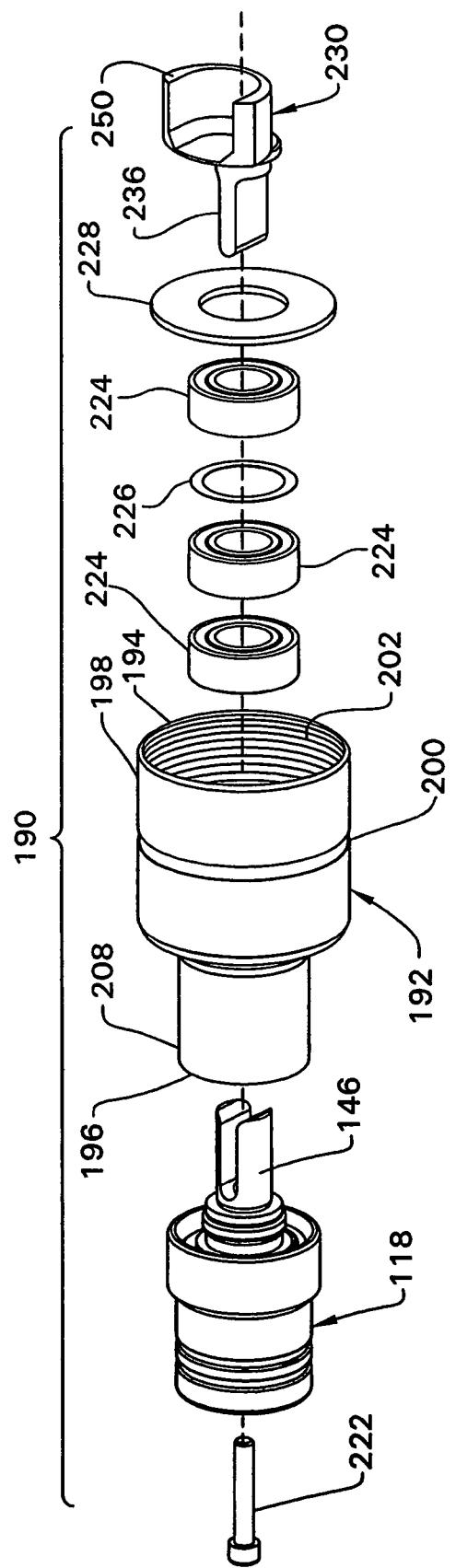
FIG. 20 is an enlarged, partially exploded perspective view of the oscillator assembly of the handpiece apparatus.

The chuck subassembly 118 is a part of a drive assembly, and preferably an oscillator assembly 190 as illustrated in FIG. 20. The oscillator assembly 190 includes a number of elements in addition to the chuck subassembly 118, such as hollow nose cone 192.

Figure 21:
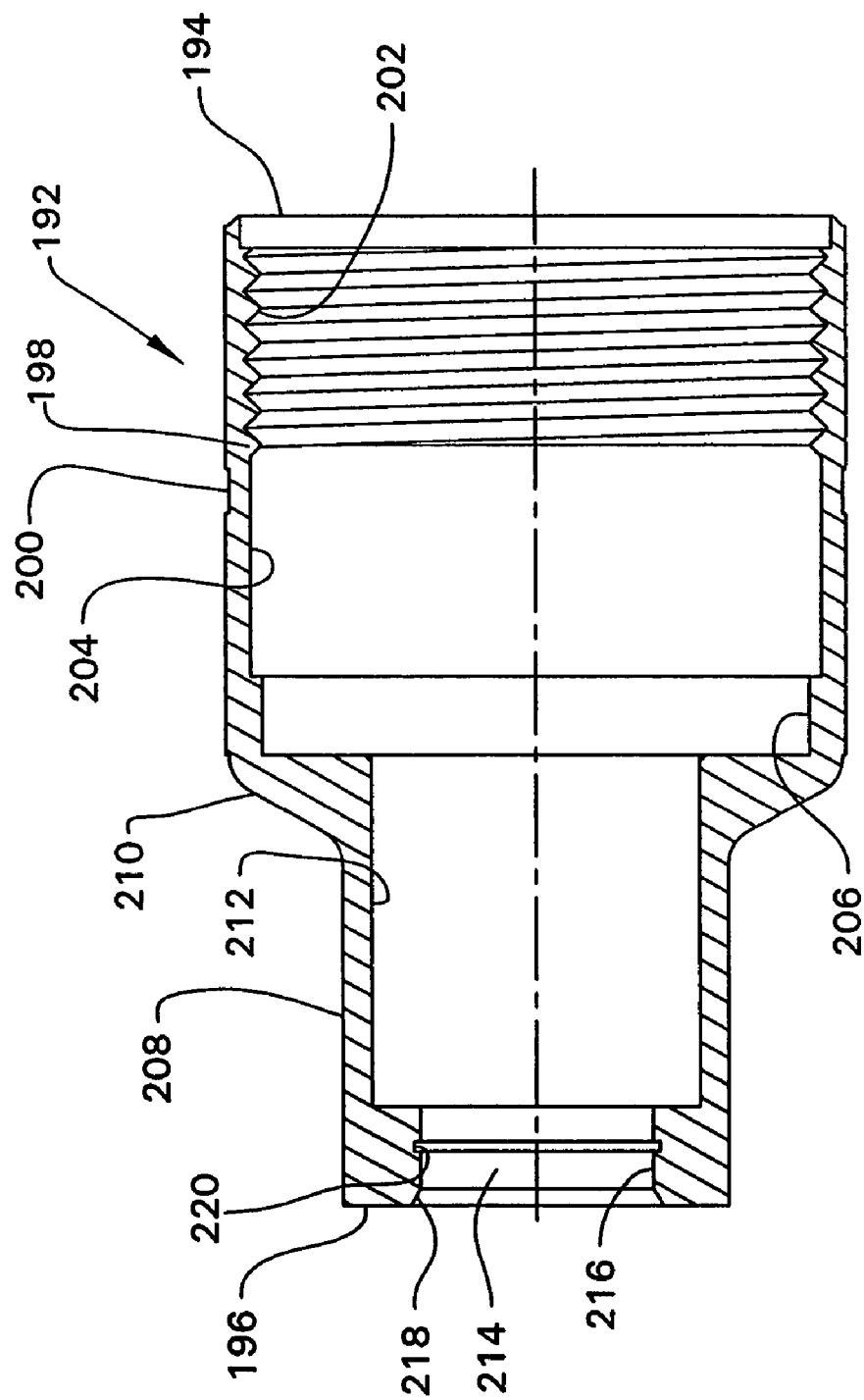
FIG. 21 is an enlarged, longitudinal cross-sectional view of the nose cone of the oscillator assembly of FIG. 20.

The nose cone 192 illustrated in FIG. 21 has a proximal end 194 and a distal end 196. A main cone section 198 that extends to the proximal end 194 has a substantially constant outer diameter except for a radially inwardly projecting annular slot 200 extending about an outer circumference of the nose cone 192. As shown in FIG. 21, inner threads 202 extend distally from the proximal end 194 about the interior of the main cone section 198. The interior of the main cone section 198 includes a receiving part wall 204 having a first diameter and a receiving stepped wall 206 having a second diameter that is less than the first diameter. The receiving part wall 204 is located axially between the threads 202 and the stepped wall 206.

The nose cone 192 includes a distal cone section 208 and an outwardly tapered cone section 210 located axially between and joining the distal cone section 208 and the main cone section 198.

The interior of the tapered cone section 210 and a part of the distal cone section 208 integral therewith define an inner wall 212 having a constant diameter along the axial length thereof. The inner wall 212 opens into a chamber defined by the receiving stepped wall 206 of the main cone section 198.

A passage 214 at the distal end 196 of the distal cone section 208 has a smaller diameter than the inner wall 212 and the other parts of the interior of the nose cone 192. The passage 214 is defined by an inner wall 216 of distal cone section 208 having a constant diameter and an outwardly flared face 218 at the distal end thereof. A radially outwardly projecting annular groove 220 is located in the passage wall 216.

The oscillator assembly illustrated in FIG. 20 further includes a cap screw 222, a pair of annular bearings such as ball bearings 224, a shim ring 226, a third annular bearing such as ball bearing 224, a washer 228 and an oscillator 230.

The oscillator 230 illustrated in FIGS. 22-25 has a proximal end 232 and a distal end 234, and an oscillator shaft member 236 at the distal end 234. The oscillator shaft member 236 has a generally rectangular and flat configuration and defines a central longitudinal axis 238 (shown in FIG. 24). A closed threaded bore 240 shown in FIG. 23 and represented by broken lines in FIGS. 22 and 24 extends axially into the shaft member 236 along the central axis 238.

The oscillator 230 includes a first cylindrical stepped part 242 joined to shaft member 236 and having a diameter substantially the same as the greatest width of shaft member 236. Opposite parallel sides of shaft member 236 taper outwardly and curvedly join the first stepped part 242 as shown in FIG. 22.

An annular groove 243 extending about the circumference of the oscillator 230 is located between the first stepped part 242 and a second stepped part 244. The second stepped part 244 has a greater diameter than the first stepped part 242.

The oscillator 230 includes a generally barrel-shaped receiver 246 having a distal end which is integral with the second stepped part 244. The barrel-shaped receiver 246 opens at the proximal end of the oscillator 230. The barrel-shaped receiver 246 includes an arcuate side wall 250 and an end wall 248 oriented transversely relative to the side wall 250 and joining the second stepped part 244. The side wall 250 defines a partially-elliptically-shaped opening.

The end wall 248 and side wall 250 define inner wall surfaces that are transverse with respect to each other. A tapered wall 252 disposed within the opening of the barrel-shaped receiver 246 joins the end wall 248 and the side wall 250.

As shown in FIG. 24, a central axis 254 of the barrel-shaped receiver 246 is parallel to, but offset from the central axis 238 of the oscillator shaft member 236.

The oscillator assembly 190 shown in FIG. 20 is assembled as follows. The chuck subassembly 118 is axially received into the distal end 196 of the nose cone 192 a short distance. As shown in FIG. 27, an inner face at the end of the distal cone section 208 radially aligns with the quad seal 182 of the chuck subassembly 118. The annular bearings 224 and the shim ring 226 are axially inserted onto and over the prongs 146 of the chuck 120 and into the bore defined by inner wall 212 of distal cone section 208. The washer 228 then is received by the stepped wall 206 of the nose cone 192. The oscillator 230 is axially inserted into the nose cone 192. The oscillator shaft member 236 has a shape that corresponds to the gap between the prongs 146 of the chuck 120. Further, the first stepped part 242 of the oscillator 230 where it joins the shaft member 236 has a curvature which conforms to the curvature of the tips 148 of the prongs 146.

The cap screw or fastener 222 inserts through the distal end of the chuck 120 and passes through the aperture 150 which is in axial alignment with the closed threaded bore 240 of the oscillator 230. The screw 222 is threaded into bore 240 so that the chuck 120 and the oscillator 230 are fixed to one another. At this stage, the oscillator assembly 190 is a complete unit.

Housing

Figure 26:
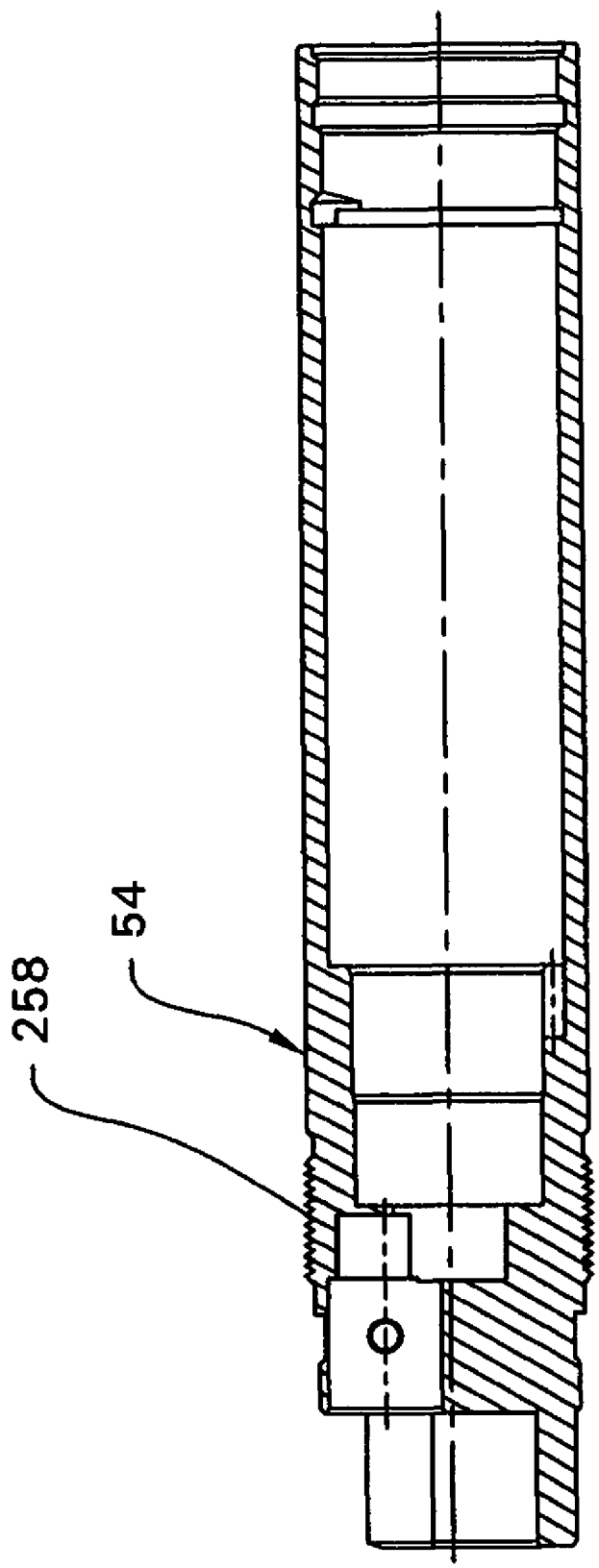
FIG. 26 is a longitudinal cross-sectional view of the housing illustrated in FIG. 1.

FIG. 26 shows a cross-sectional view of the hollow housing 54 in isolation with no assemblies located therein. The housing 54 is dimensioned to snugly receive and support the various assemblies therein. Threads 258 are located on outer face of housing 54 which threadingly engage threads 202 of nose cone 192. The end of the housing 54 contacts one side of washer 228 when the nose cone 192 is secured to the housing. The other side of the washer 228 contacts the bearing 224 to seat or fix the bearing and thus the oscillator assembly 190 thereof relative to the housing 54.

Assembly of Surgical Handpiece

The surgical handpiece illustrated in FIG. 1 is assembled as follows. The extension gear assembly 55 and the cutter motor assembly 50 are inserted into the proximal end of the housing 54. As illustrated in FIG. 3, when positioned in the housing 54, the internal gear teeth 67 at the proximal end 66 of the extension gear shaft 56 mesh with and are driven by the motor output shaft 53 of the cutter motor assembly 50. Further, when positioned in the housing 54, the radially projecting flange 73 of the flanged bearing 72 seats against a stepped inner surface of the housing 54. Thus, the seated flange 73 assists in maintaining the extension gear assembly 55 at a proper location within the housing 54. Retaining ring 48 joins the cable assembly piece 42 to the proximal end of the housing 54. The cable assembly piece 42 closes the proximal end of the housing 54.

The eccentric gear assembly 75 shown in FIG. 3 inserts axially into the distal end of the housing 54. The eccentric gear assembly 75 is supported in the housing 54 so that the teeth 80 at the proximal end thereof mesh with the teeth 58 at the distal end 57 of the extension gear shaft 56 for rotation therewith.

The oscillator assembly 190 is then joined to the distal end of the housing 54 by screwing the nose cone 192 onto the threads 258 of the housing to close the handpiece apparatus 40. When closed, the barrel 110 of the eccentric gear assembly 75 is positioned in the barrel receiver 246 of the oscillator assembly 190.

Cutting Accessory

The handpiece apparatus 40 according to the invention is typically utilized with a cutting accessory. One such cutting accessory is an elongate cutting accessory 260 as shown in FIGS. 29-31. As shown in FIG. 30, the cutting accessory 260 defines a longitudinal axis 262. The cutting accessory 260 includes a proximal end 264 and a distal cutting end 266. As shown in FIG. 31, an elongate locking tab 268 at the proximal end 264 of the cutting accessory 260 has a generally rectangular cross-section with rounded edges. The modified cutting assembly includes detent openings 270 formed in the locking tab 268.

The cutting accessory 260 includes a cylindrical shaped solid base 272 and a hollow cylindrical receiver 274. The solid base 272 is positioned axially between and is integral with the locking tab 268 and the cylindrical receiver 274.

In the illustrated embodiment, the hollow receiver 274 has an outer diameter that is greater than the diameter of the solid base 272, and a length that is greater than the combined length of the locking tab 268 and the base 272. The hollow receiver 274 defines a cylindrical chamber 275 extending the length thereof. At the distal cutting end 266 of the receiver 274, cutting teeth 276 project axially outwardly. The cutting teeth 276 extend about the circumference of the distal end 266 of the receiver 274, except for at a tapered end face 278 illustrated in FIG. 29. The tapered end face 278 angles inwardly from the outer surface of receiver 274 so as to define a depression in the distal cutting end 266. As shown in FIG. 29, a longitudinally oriented elongate window 282 is formed along a portion of the hollow receiver 274 to provide access to inner areas of the chamber 275.

While the preferred cutting accessory is a bone plug cutter or other bone harvesting tool, it will be appreciated that other types of surgical tools may be utilized.

Mounting Cutting Accessory to Handpiece

The cutting accessory 260 is mounted to the chuck subassembly 118 as follows. The collar 152 is moved against the biasing force of the coil spring 176. Axial movement of the collar 152 in the above manner exposes the distal end 124 of the chuck 120. The collar 152 is only capable of moving a predetermined distance in the proximal direction, so that balls 186 are maintained in the apertures 132, 134. This predetermined axial distance is defined by the axial distance between stop shoulder 159 defined on collar 152 and washer 178 when the collar 152 is in its resting position. The slots 170 have substantially the same diameter therealong and thus the cooperation of the closed apertures 132, slots 170 and the respective balls 186 allow axial movement of collar 152 relative to chuck 120 while preventing rotating movement of the collar 152 relative to the chuck 120. Further the closed ends of the slots 170 act in combination with the balls 186 to prevent the spring 176 from forcing the collar 152 from the end of the handpiece apparatus 40.

Movement of the collar 152 proximally with respect to the balls 186 positioned in the open apertures 134 of the chuck 120 and the respective slots 172 permits the balls 186 to enter into the larger diameter slot portion 173 of the respective slots 172. Thus, the respective balls 186 are free to move radially outwardly and away from the inner chamber of the chuck 120.

The cross-sectional shape of the locking tab 268 of the cutting accessory 260 shown in FIG. 31 conforms to the opening defined by the side and end walls 130, 131 of the receiving part 126 of the chuck 120. When the locking tab 268 is placed in the receiving part 126 with the collar 152 pulled back in the proximal direction, the balls 186 in the open bore apertures 134 are forced radially outwardly and into respective slot portions 173 having a greater diameter.

When the cutting accessory 260 is completely inserted in the chuck 120, the detents 270 in the locking tab 268 are circumferentially aligned with the respective balls 186 located in open apertures 134. The collar 152 is then released and moves in the distal direction due to the force of the coil spring 176. Movement of the collar 152 distally effectively positions the balls 186 (located in open apertures 134) in the smaller diameter slot portions 174 so as to force balls 186 radially inwardly and into the locking tab detents 270. Thus, the cutting accessory 260 is locked axially in the chuck 120.

Operation

The handpiece apparatus 40 operates as follows. A well known control mechanism, such as a switch (not shown) is operated to control the cutter motor assembly 50. The cutter motor assembly 50 rotates motor output shaft 53. The motor output shaft 53 is coupled to the extension gear assembly 55 and thus rotates the extension gear shaft 56. The extension gear shaft 56 has gear teeth 58 that mesh with gear teeth 80 of the eccentric gear shaft 78, and thus rotation of the motor output shaft 53 is transferred to the eccentric gear shaft 78. The longitudinal axis 95 of the eccentric gear shaft portion 92 is offset from the central longitudinal axis 93 of the central portion 88 of the eccentric gear shaft 78. Thus, when the eccentric gear shaft 78 is rotated, the barrel 110 mounted at the distal end to the eccentric gear shaft portion 92 rotates about an orbital path.

As shown in FIGS. 28A-28D, the barrel 110 at the distal end of the eccentric gear shaft 78 is received within the barrel receiver 246 of the oscillator 230. The convex shape of the barrel 110 provides a line or point contact between the barrel and the barrel receiver 246, which reduces friction and assists in minimizing wear. The orbital path 285 traveled by the barrel 110 causes the barrel receiver 246 of the oscillator 230 to oscillate angularly about the central longitudinal axis 238 of the oscillator shaft member 236. The radius of the barrel receiver 246 is greater than the radius of the barrel 110 by a predetermined amount enabling movement of the barrel about the interior within the receiver to the positions shown in FIGS. 28A-28D. Since the chuck 120 is fixed to the oscillator 230 by the cap screw 222, the cutting accessory 260 mounted in chuck 120 also oscillates about the longitudinal axis 262 of the cutting accessory, which axis 262 is aligned with the longitudinal axis 238, to provide a cutting action.

$2^{nd}$ Embodiment

FIGS. 32 and 33 illustrate a second embodiment of the invention. The same reference numerals are used for components which are similar or identical to components of the first embodiment. In the first embodiment, the cutting accessory 260 is aligned with the central longitudinal axis of the handpiece 40. In the second embodiment shown in FIG. 32, the chuck subassembly 118 has a central longitudinal axis 290 about which the cutting accessory 260 oscillates, that is located eccentrically from the central longitudinal axis 292 of the handpiece.

In the embodiment of FIGS. 32 and 33, the extension gear assembly 55 has been removed. Although, the nose cone 192 no longer has a symmetrical shape, the nose cone threads onto the housing 54 as the parts contained therein rotate with the nose cone.

In this embodiment, the motor output shaft 53 is directly connected to the eccentric gear shaft 78 and has the same axis of rotation 292 as the central cylindrical portion 88 of the eccentric gear shaft 78. As in the first embodiment, the barrel 110 within the barrel receiver 246 of the oscillator 230 follows the orbital path 285. Since the longitudinal central axis 290 for both the oscillator 230 and the chuck subassembly 118 is offset from center of the orbital path 285, the rotational movement of the barrel 110 is converted into oscillation of the cutting accessory 260 about the chuck subassembly central axis 290.

Although a particular preferred embodiment of the invention is disclosed in detail for illustrative purposes, it will be recognized that variations or modifications of the disclosed apparatus, including the rearrangement of parts, lie within the scope of the present invention.

What is claimed is:

1. A surgical cutting apparatus comprising:
   an elongate hollow housing with a proximal end and a distal end;
   a cutter power assembly located at the proximal end of the housing;
   an eccentric output assembly positioned in the housing and comprising a single eccentric shaft having a first end rotatably driven by said cutter power assembly, an opposing second end of said eccentric shaft arranged to travel about an orbital path when the eccentric shaft is driven;
   an oscillator assembly including an oscillator having an oscillator output shaft, the oscillator assembly located toward the distal end of the housing from the eccentric output assembly, said oscillator assembly coacting with the second end of said eccentric shaft so that in response to travel of the second end about the orbital path, said oscillator rotatably oscillates back and forth about a central longitudinal axis of said oscillator output shaft; and
   a chuck assembly located at the distal end of the housing comprising a chuck for mounting at a first end to said oscillator, said chuck having an opening at a second end for receiving a cutting accessory, said chuck assembly fixedly securing the cutting accessory to said chuck, whereby the chuck and the cutting accessory have a common longitudinal axis along the lengths thereof,
   wherein, in response to movement of the second end of the single eccentric shaft about the orbital path, the chuck and the cutting accessory oscillate rotatably back and forth about the common longitudinal axis of the chuck and the cutting accessory; and
   wherein the longitudinal axis of said chuck is common with the central longitudinal axis of said oscillator output shaft.

2. The cutting apparatus according to claim 1, wherein said eccentric output assembly further comprises a single barrel mounted to the second end of said eccentric shaft.

3. The cutting apparatus according to claim 2, wherein said oscillator assembly includes a receiver for receiving said barrel, said receiver having a radius greater than the radius of said barrel by a predetermined amount so that said barrel is capable of moving about the orbital path within said receiver, with said receiver pivoting back and forth about the oscillator output shaft thereof.

4. The cutting apparatus according to claim 2, wherein said barrel is supported on said eccentric shaft by ball bearings on said second end of said eccentric shaft.

5. The cutting apparatus according to claim 1, further comprising a nose cone for receiving said oscillator assembly therein, said nose cone being secured to the distal end of the elongate housing, and wherein said cutting accessory comprises an elongate cutting accessory having a first end received in the opening at the second end of the chuck.

6. The cutting apparatus according to claim 1, wherein the central longitudinal axis of said oscillator output shaft is substantially parallel to and spaced from a central longitudinal axis of said housing, and wherein said cutter power assembly includes a motor and said eccentric output assembly is free from a motor.

7. The cutting apparatus according to claim 1, wherein the surgical cutting apparatus comprises a powered surgical handpiece and the cutting accessory comprises a monolithic surgical tool having a first end fixedly secured to said chuck and a second end having a cutting edge.

8. The cutting apparatus according to claim 1, wherein the cutting accessory comprises an elongate cutting accessory having a hollow receiver and a distal cutting end.

9. A surgical cutting apparatus comprising:
   an elongate hollow housing with a proximal end and a distal end;
   a cutter power assembly located at the proximal end of the housing;
   a drive assembly comprising an oscillator assembly including a driver comprising an oscillator shaft member, the oscillator shaft member having a longitudinal axis;
   a chuck assembly coacting with said drive assembly and comprising:
      a chuck having an opening for receiving a surgical tool, an outer face of said chuck having at least two radially spaced open bore apertures, and the chuck having a longitudinal axis;
      an elongate hollow collar having an opening at a first end for receiving said chuck therein, said collar having slots corresponding to said apertures on an inner surface at the first end thereof;
      balls for insertion into said apertures and for receipt in said slots; and
      a spring for biasing said collar outwardly,
   wherein applying a force at the distal end of said collar compresses said spring to enable radially outward movement of said balls and insertion of an end of a surgical tool into the opening in the chuck, the surgical tool having a longitudinal axis, and wherein release of said collar locks the surgical tool in said chuck,
   wherein operation of the cutter power assembly provides power to the oscillator assembly so that the oscillator shaft member rotatably oscillates about a longitudinal axis thereof to rotatably oscillate the chuck and the surgical tool fixedly secured to the chuck, and
   wherein the longitudinal axes of the chuck, the oscillator shaft member and the surgical tool are common axes.

10. The cutting apparatus according to claim 9, wherein the surgical cutting apparatus comprises a powered surgical handpiece.

11. The cutting apparatus according to claim 10, wherein the surgical tool comprises a bone-harvest cutter.

12. The cutting apparatus according to claim 11, wherein the bone harvest cutter comprises a bone plug removing device.

13. The cutting apparatus according to claim 9, wherein the release of the collar moves the collar axially so that each said ball bears against an inwardly stepped face within the respective slot that forces each said ball radially inwardly through the respective open one of said apertures to lock the surgical tool in the chuck.

14. The cutting apparatus according to claim 9, wherein said radially spaced apertures of said chuck further comprise a pair of closed bore apertures, and
wherein the surgical tool includes a locking tab having a detent in an outer face, each of said balls corresponding to a respective said open bore aperture extending therethough a distance sufficient to enter the detents and maintain the surgical tool in said chuck.

15. The cutting apparatus according to claim 14, wherein each said ball within the respective closed bore aperture contacts an end of the respective slot in the inner surface of the collar to prevent said collar from separating from said handpiece.

16. The cutting apparatus according to claim 9, wherein said radially spaced apertures of said chuck comprise a pair of said open bore apertures and a pair of closed bore apertures.

17. The cutting apparatus according to claim 9, wherein the opening of said chuck has a rectangular shape with rounded corners for receiving a mating locking tab of the surgical tool.

18. The cutting apparatus according to claim 9, wherein a proximal end of said surgical tool is mounted to the distal end of said chuck.

19. A surgical cutting apparatus comprising:
an elongate hollow housing with a proximal end and a distal end;
a motor assembly located at the proximal end of the housing, said motor assembly including a motor and a motor output shaft;
an eccentric output assembly disposed in the housing and comprising:
a single elongate eccentric shaft having a first shaft portion defining a central longitudinal axis at a first end thereof, said eccentric shaft configured to be rotatably driven at the first end by said motor output shaft of said motor, said eccentric shaft having a second eccentric shaft portion at an opposing second end of said eccentric shaft, the second eccentric shaft portion having a longitudinal projecting axis that is substantially parallel to and spaced from the central longitudinal axis of said first shaft portion, wherein rotation of said eccentric shaft moves said second eccentric shaft portion about an orbital path; and
a transfer member mounted to the second eccentric shaft portion, the transfer member being movable about the orbital path;
an oscillator assembly located toward the distal end of the housing from the eccentric output assembly comprising:
an oscillator formed by an oscillator shaft member at a first end and a receiver for receiving the transfer member at a second end, said oscillator shaft member having a longitudinal axis that is parallel to the central longitudinal axis of said first shaft portion of said eccentric shaft; and
a nose cone for receiving said oscillator therein, said nose cone being secured to the distal end of the elongate hollow housing;
and,
a chuck assembly located at the distal end of the housing comprising an elongate chuck for mounting at a proximal end to said oscillator assembly, said chuck having an opening at a distal end for receiving a cutting accessory and said chuck having a longitudinal axis,
wherein operation of said motor rotates said eccentric shaft to move said transfer member about the orbital path so that said oscillator shaft member of said oscillator oscillates about the longitudinal axis thereof by pivotally rotating in a first direction about the longitudinal axis thereof and subsequently pivotally rotating in a second opposing direction about the longitudinal axis thereof, the oscillation of said oscillator shaft member comprising periodically changing between the first and second directions so that said chuck secured thereto rotatably oscillates about the longitudinal axis of said chuck, and an elongate cutting accessory fixedly mounted to the distal end of said chuck and rotatably oscillating with the chuck about a longitudinal axis of the cutting accessory.

20. The cutting apparatus according to claim 19, said apparatus further comprising:
a gear extension assembly mounted in said housing comprising an extension gear shaft with a first end that is adapted to receive an end of the motor output shaft and a second end oriented toward the distal end of said housing, the second end having an extension gear projecting radially outwardly from a longitudinal axis of the extension gear shaft,
wherein the longitudinal axis of said extension gear shaft corresponds to the longitudinal axis of said motor output shaft and is substantially axially centered in said elongate housing.

21. The cutting apparatus according to claim 20, wherein the first end of said eccentric shaft includes a gear projecting radially outwardly from the longitudinal axis of the eccentric shaft to mesh with teeth of the extension gear, and wherein said eccentric output assembly is free from a motor and said gear extension assembly is free from a motor.

22. The cutting apparatus according to claim 21, wherein the longitudinal axis of said eccentric shaft is substantially parallel to and spaced from the longitudinal axis of said extension gear shaft.

23. The cutting apparatus according to claim 22, wherein a longitudinal axis of said oscillator shaft member comprises substantially the same axis as the longitudinal axis of said extension gear shaft.

24. The cutting apparatus according to claim 19, said apparatus further comprising:
a gear extension assembly mounted in the housing and having an extension gear shaft with a first end that is driven by the motor output shaft and a second end oriented toward the distal end of said housing, the second end having an extension gear projecting radially outwardly from a longitudinal axis of the extension gear shaft,
wherein the longitudinal axis of said extension gear shaft is parallel to and spaced from the longitudinal axis of said motor output shaft, the longitudinal axis of said motor output shaft being substantially axially centered in said elongate housing.

25. The cutting apparatus according to claim 24, wherein a longitudinal axis of said oscillator shaft member is substantially parallel to and spaced from the longitudinal axis of said housing, and wherein the longitudinal axis of said chuck is substantially parallel to and common with the longitudinal axis of said cutting accessory.

26. The cutting apparatus according to claim 19, said chuck assembly comprising:
a mounting element at a second end of said chuck for mounting to said shaft member of said oscillator, an outer face of said chuck having equidistant and radially spaced apertures spaced radially about a circumference of an outer surface thereof;
an elongate hollow collar having openings at opposing ends thereof, an opening at a first end for receiving said chuck therein, said collar having equidistantly spaced slots on an inner surface at the first end thereof, said slots corresponding to said apertures of said chuck;
balls for insertion into said apertures and for receipt in said slots, said balls having a diameter greater than the diameter of said apertures; and
a spring for positioning against an inner lip of said collar to bias said collar axially outwardly to at least enclose or extend beyond the distal end of said chuck.

27. The cutting apparatus according to claim 26, wherein applying a force at the distal end of said collar and toward said housing compresses said spring to enable viewing of said chuck and insertion of an end of a cutting accessory into the opening in the chuck, and
wherein release of said collar extends the collar distally whereby said balls bear against a surface of said slot so that at least two of said balls move inwardly through at least two respective open ones of said apertures to lock a cutting accessory in said chuck.

28. The cutting apparatus according to claim 26, said chuck assembly further comprising a washer and retainer in alignment with a proximal end of said spring for retaining said spring in said collar of said chuck.

29. The cutting apparatus according to claim 19, wherein the cutter power assembly includes a powered drive shaft that rotates in a single direction about the longitudinal axis thereof, and wherein the oscillator assembly converts the rotational motion of the cutter power assembly into the oscillation of the oscillator shaft about the longitudinal axis of the oscillator shaft.

30. The cutting apparatus according to claim 19, wherein the cutting apparatus comprises an elongate powered surgical handpiece and the cutting accessory comprises a monolithic surgical tool having a first end received in the opening at the distal end of the chuck and a second end having a cutting edge.

31. A cutting apparatus comprising:
an elongate hollow housing with a proximal end and a distal end;
a cutter power assembly located at the proximal end of the housing, said cutter power assembly including a power output shaft;
an oscillator assembly mounted in the housing comprising an oscillator having a shaft member with a mating projection, said oscillator being oriented toward the distal end of the elongate housing;
a linking assembly mounted in the housing, said linking assembly linking said power output shaft to said oscillator; and
a chuck assembly comprising:
a chuck with a mounting element having a pair of prongs at a first proximal end of the chuck for receiving therebetween said mating projection of said shaft member of said oscillator and an opening at a second distal end for receiving a cutting accessory, an outer face of said chuck having equidistant and radially spaced apertures;
an elongate annular hollow collar having openings at opposing ends thereof, an opening at a first end for receiving said chuck therein, said collar having equidistantly spaced axially oriented slots on an inner surface at the first end thereof, said slots corresponding to said apertures;
balls for insertion into said apertures and for receipt in said slots; and
a spring for positioning against an inner lip of said collar to bias said collar outwardly to at least enclose or to extend beyond the distal end of said chuck,
wherein applying a force at the distal end of said collar compresses said spring to enable viewing of said chuck and insertion of an end of a cutting accessory into the opening in the chuck, wherein release of said collar extends the collar distally whereby said balls bear against a surface of said slot so that at least two of said balls move inwardly through at least two respective open ones of said apertures to engage in detents of a locking tab of a cutting accessory to lock the cutting accessory in said chuck.

32. The cutting apparatus according to claim 31, including a screw, wherein said chuck has an open bore aperture along a center axis thereof opening between said pair of prongs, and said shaft member of said oscillator has a corresponding threaded bore in the mating projection located along the central axis thereof, wherein said screw mounts through said chuck and into said bore of the mating projection of the oscillator to secure the chuck assembly to said oscillator assembly and maintain said chuck assembly on the cutting apparatus.

33. The cutting apparatus according to claim 31, wherein the opening of said chuck has a rectangular shape with rounded corners for receiving a mating locking tab of a cutting accessory.

34. The cutting apparatus according to claim 31, wherein said chuck assembly further comprises a washer and retainer in alignment with a proximal end of said spring for retaining said spring in said collar of said chuck.

35. The cutting apparatus according to claim 31, wherein said oscillator comprises said shaft member at a first end and further comprises a barrel receiver at a second end, said barrel receiver projecting substantially radially from the longitudinal axis of said shaft member and having a cylindrical shape at a proximal end.

36. The cutting apparatus according to claim 35, comprising a nose cone for receiving said oscillator, said nose cone being secured to the distal end of said housing and wherein said oscillator assembly further comprises bearings and a support washer for rotatably supporting said shaft member in said nose cone.

37. The cutting apparatus according to claim 31, wherein at least two of the equidistantly spaced slots on the inner surface of said collar have a slot portion with a depth adjacent an outer rim of said collar that is greater than the depth of a stepped slot portion of said slot inwardly from said outer rim, whereby when said collar is physically retracted inwardly against the force of said spring and said cutting accessory is inserted into the opening of said chuck, said balls are capable of moving radially outwardly and when said collar is released, said collar moves axially relative to said balls so that said balls seat on the respective said stepped slot portions axially inwardly from said outer rim so that the balls engage the detents of the cutting accessory in said chuck.

38. The cutting apparatus according to claim 31, said linking assembly linking the output of said motor to said oscillator comprising an eccentric gear assembly mounted in said housing and comprising:

an elongate eccentric gear shaft having a gear shaft portion defining a central longitudinal axis at a first end thereof, said eccentric gear shaft arranged to be driven at the first end by said power output shaft, said eccentric gear shaft having a second eccentric gear shaft portion at an opposing second end of said eccentric gear shaft, the eccentric gear shaft portion having a projecting axis that is parallel to and spaced from the central longitudinal axis of said eccentric gear shaft, whereby rotation of said eccentric gear shaft moves said eccentric gear shaft portion about an orbital path with respect to the central longitudinal axis; and a single barrel member-mounted to the second eccentric gear shaft portion, the single barrel member being movable about the orbital path, wherein said oscillator comprising said shaft member at a distal end, further comprises a barrel receiver at a proximal end, said barrel receiver receiving said barrel member that is movable about the orbital path to pivotally oscillate said shaft member of said oscillator back and forth about the longitudinal axis of said shaft member.

39. The cutting apparatus according to claim 31, wherein the cutting apparatus comprises a powered surgical handpiece and the cutting accessory comprises a monolithic surgical tool having a cutting edge at a distal end thereof, wherein the surgical tool comprises an elongate hollow surgical tool having an opening at the distal end thereof.

\* \* \* \* \*